(12) United States Patent
Borén et al.

(10) Patent No.: US 8,025,880 B2
(45) Date of Patent: Sep. 27, 2011

(54) IMMUNOGLOBULIN AGAINST HELICOBACTER PYLORI

(75) Inventors: Thomas Borén, Umeå (SE); Lennart Hammarström, Huddinge (SE)

(73) Assignee: Helicure AB, Umea (SE)

( * ) Notice: Subject to any disclaimer, the term of this patent is extended or adjusted under 35 U.S.C. 154(b) by 483 days.

(21) Appl. No.: 12/072,429

(22) Filed: Feb. 26, 2008

(65) Prior Publication Data

US 2008/0213224 A1 Sep. 4, 2008

Related U.S. Application Data

(60) Provisional application No. 60/904,241, filed on Mar. 1, 2007.

(51) Int. Cl.
*A61K 39/00* (2006.01)
*A61K 39/395* (2006.01)
*A61K 39/38* (2006.01)

(52) U.S. Cl. ............ 424/139.1; 424/130.1; 424/135.1; 424/164.1; 424/184.1; 530/350; 530/367.1; 530/387.3; 530/388.4

(58) Field of Classification Search ............ 424/130.1, 424/135.1, 139.1, 164.1, 184.1; 530/350, 530/387.1, 387.3, 388.4
See application file for complete search history.

(56) References Cited

U.S. PATENT DOCUMENTS 5,260,057 A 11/1993 Cordle
2004/0234529 A1 11/2004 Boren

FOREIGN PATENT DOCUMENTS

EP 0484 148 A1 6/1992
WO WO 97/47646 12/1997

OTHER PUBLICATIONS

Hennig, E.E., et al. Infection and Immunity, vol. 72, No. 6, pp. 3429-3435, Jun. 2004.*
Boren et al., Attachment of *Helicobacter pylori* to Human Gastric Epithelium Mediated by Blood Group Antigens, Science 262:1892-1895, 1993.
Dubel et al., A family of vectors for surface display and production of antibodies, Gene 128:97-101, 1993.
Gustafsson et al, Carbohydrate-dependent inhibition of *Helicobacter pylori* colonization using porcine milk, Glycobiology 16:1-10, 2006.
Hennig et al., Heterogeneity among *Helicobacter pylori* Strains in Expression of the Outer Membrane Protein BabA, Infection and Immunity 72:3429-3435, 2004.
Johansson et al., Efficient expression of recombinant human monoclonal antibodies in *Drosophila* S2 cells, J. Immunol. Methods 318:37-46, 2007.
Kimmel et al., Identification of Immunodominant Antigens from *Helicobacter pylori* and Evaluation of Their Reactivities with Sera . . . , Infection and Immunity 68:915-920, 2000.
Kruger et al., In situ delivery of passive immunity by lactobacilli producing single-chain antibodies, Nature Biotechnology 20:702-706, 2002.

* cited by examiner

*Primary Examiner* — Rodney P. Swartz
(74) *Attorney, Agent, or Firm* — Lynn E Barber

(57) ABSTRACT

The present invention relates to materials and methods for prevention, treatment and diagnosing of infections caused by *Helicobacter pylori* (*H. pylori*). More specifically the present invention relates to new specific variable antibody regions, derivatives thereof and the fully human immunoglobulin, Abba3, which exhibit specific activity to the BabA antigen, expressed by *H. pylori*, methods for the production of said immunoglobulins, their isolation and use, for example in detection of disease causing *H. pylori*. The present invention also relates to immunization therapies, i.e. passive vaccination for the treatment and prevention of pathologic infections caused by *H. pylori* strains.

3 Claims, 12 Drawing Sheets

Fig.2:

(a) VH-regions:

```
                  1              FR1               26    CDR1     39         FR2         55    CDR2
SEQ ID NO:20      EVQLVESGGGLVQPGGSLRLSCAAS   GFTFSSYE   MNWVRQAPGKGLEWVSY   ISSSGSTI
SEQ ID NO:18      Q------IG------A-E-        ----NLF-   -A------QS--VI--    -G-----T
SEQ ID NO:21      Q------IG------A-E-         ----NLF-   -A------QG--VI-    -G-----T
SEQ ID NO:22      Q------AW------EV-          --P-NL--   --I----------IA-    -G---TLM

66              FR3              104    CDR3                              IgHG1
SEQ ID NO:20      YYADSVKGRFTISRDNAKNSLYLQMNSLRAEDTAVYYC   AR............   ..........    WGQGTLVAVSS
SEQ ID NO:18      R-----IV-----DKE-MF---L-S--VD----T-F-   --LNGWAGSGLDH                   WGQGTLVAVSS
SEQ ID NO:21      R-----IV-----DKE-MF---L-S--VD----T-F-   --LNGWAGSGLDH                   WGQGTLVAVSS
SEQ ID NO:22      K---------S-----------HL--PEV-----I--   --FNGWSGSGLDY                   WGQGTLVSVSS

1              FR1               26    CDR1     39         FR2         55    CDR2
SEQ ID NO:23      QVQLVQSGAEVKKPGASVKVSCKAS   GYTFTSYG   ISWVRQAPGQGLEWMGW   ISAYNGNT
SEQ ID NO:24      ------Q------T-----------    --D-KAH-   -M--------------P   ---GN-Y-

66              FR3              104    CDR3                              IgHG1
SEQ ID NO:23      NYAQKLQGRVTMTTDTSTSTAYMELRSLRSDDTAVYYC   AR............   ..........
SEQ ID NO:24      T---SVR-----V-----T-V----KN-------F-    --DQGGSRFGELLILDY                WGQGTLVTVSS
```

Fig.2:

(b) VL-regions

```
                    1           FR1                  26  CDR1   QSISSY  39  FR2   LNWYQQKPGKAPKLLIY  55  CDR2   AAS
SEQ ID NO:25        DIQMTQSPSSLSASVGDRVTITCRAS       ------   ------           -----------------      ---
SEQ ID NO:19        --------------------------       ------   ------           -T--NN-----------      ---
SEQ ID NO:26        --------------------------       ---Q--   --D-N-           -----------------      -Y-
SEQ ID NO:27        --V-----------------------       ------   ------           -----------------      ---

65          FR3                               104 CDR3          114 FR4              C-Kappa
SEQ ID NO:25        SLQSGVPSRFSGSGSGTDFTLTISSLQPEDFATYYC QQSYSTP..      FGQGTKVEIK RTVAAPS ..........
SEQ ID NO:19        -----------------------------------  --------LWT    FGGGTKVDIK RTVAAPS
SEQ ID NO:26        ---G-------------------------------  -----P-LT     FGGGTKVDIK RTVAAPS
SEQ ID NO:27        -----------------------------------  ------LT      FGGGTKVEIK RTVAAPS 1           FR1                  26  CDR1   QSLVYSDGNTY 39 FR2  LNWFQQRPGQSPRRLIY  55  CDR2   KVS
SEQ ID NO:28        DVVMTQSPLSLPVTLGQPASISCRSS       ------   -----------      -----------------      ---
SEQ ID NO:29        --------------------------       --S---   -G---L-----      ------R----A-----      -R--

65          FR3                               104 CDR3          114 FR4              C-Kappa
SEQ ID NO:28        NRDSGVPDRFSGSGSGTDFTLKISRVEAEDVGVYYC MQGTHWP..      FGQGTRVEIK RTVAAPS ..........
SEQ ID NO:29        -----------------------------------  ------WT      FGQGTRVEIK RTVAAPS
```

Fig.2 (cont.):

(b) VL-regions

```
                        1         FR1          26  CDR1    39       FR2         55
             CDR2
SEQ ID NO:25   DIQMTQSPSSLSASVGDRVTITCRAS QSISSY LNWYQQKPGKAPKLLIY
AAS
SEQ ID NO:19   -------------------------- ------ -----------------
---
SEQ ID NO:26   -------------------------- -T--NN ------Y----
------ ---
SEQ ID NO:27   --V-----------------Q-- -D--N- -----------------
---

65              FR3           104  CDR3    114
        FR4     C-Kappa

SEQ ID NO:25   SLQSGVPSRFSGSGSGTDFTLTISSLQPEDFATYYC QQSYSTP..
.......... .......
SEQ ID NO:19   ----------------------------------- ------LWT
FGQGTKVEIK RTVAAPS
SEQ ID NO:26   ---G------------------------------- -----P-LT
FGGGTKVDIK RTVAAPS
SEQ ID NO:27   ----------------------------------- -------LT
FGGGTKVEIK RTVAAPS

1         FR1          26  CDR1    39       FR2
        55 CDR2

SEQ ID NO:28   DVVMTQSPLSLPVTLGQPASISCRSS QSLVYSDGNTY
LNWFQQRPGQSPRRLIY KVS
SEQ ID NO:29   -----------------S-------- -G---L----N ----R-----A-
----- R--

65              FR3           104  CDR3    114
        FR4    C-Kappa

SEQ ID NO:28   NRDSGVPDRFSGSGSGTDFTLKISRVEAEDVGVYYC MQGTHWP..
.......... .......
SEQ ID NO:29   ----------------------------------- -------WT
FGQGTRVEIK RTVAAPS
```

Fig. 10

| Strain | Abba3-Ab Immunoblot | Abba3-Ab ELISA | Biot-Leb ELISA | Leb/ALeb |
|---|---|---|---|---|
| 17875/leb | +++ | +++ | +++ | 1.3 |
| J 99 | + | ++ | ++ | 1.6 |
| Sw 8 | +++ | ++ | +++ | 1 |
| Sw 21 | ++ | ++ | ++ | 0.9 |
| Sw 44 | +++ | ++ | +++ | 1.4 |
| Sw 53 | +++ | ++ | ++ | 1 |
| Sw 60 | ++ | + | + | 2.5 |
| Sw 63 | ++ | ++ | ++ | 0.9 |
| Sw 64 | ++ | ++ | ++ | 0.8 |
| Sw 66 | + | ++ | ++ | 1 |
| Sw 68 | ++ | ++ | ++ | 1.2 |
| Sw 99 | -+ | ++ | ++ | 1 |
| Sw 103 | +++ | ++ | ++ | 2.7 |
| Sw 105 | ++ | ++ | +++ | 0.8 |
| Sw 110 | ++ | +++ | +++ | 0.9 |
| Sw 126 | ++ | ++ | ++ | 0.9 |
| A 703 | +++ | +++ | +++ | 0.7 |
| A 722 | ++ | +++ | +++ | 0.9 |
| A 723 | - | -- | ++ | 8.8 |
| P 302 | + | + | + | 15.6 |
| P 304 | ++ | ++ | + | 17.8 |
| P 306 | ++ | ++ | ++ | 1.2 |
| P 308 | ++ | + | ++ | 6.7 |
| P 314 | -- | -- | + | 17.5 |
| P 315 | -- | -- | + | 22.1 |
| P 318 | -- | -- | +++ | 61.6 |
| P 320 | -- | --- | + | 22.5 |
| P 322 | ++ | +++ | +++ | 1.5 |
| P 323 | +++ | ++ | ++ | 1.2 |
| P 325 | -- | -- | ++ | 14.8 |
| P 326 | + | ++ | + | 4.6 |
| P 328 | ++ | ++ | ++ | 1.2 |
| P 330 | ++ | +++ | +++ | 51 |
| P 331 | -- | - | ++ | 90.4 |
| P 433 | +++ | +++ | ++ | 0.8 |
| P 434 | ++ | ++ | ++ | 0.8 |
| P 442 | -- | -- | ++ | 8.1 |
| P 445 | + | ++ | ++ | 14.4 |
| P 449 | ++ | +++ | ++ | 11.3 |
| P 452 | -- | -- | + | 7.1 |
| P 454 | ++ | ++ | ++ | 22.1 |
| P 455 | + | ++ | ++ | 31.7 |
| S 831 | -- | -- | ++ | 70.8 |
| S 858 | ++ | +++ | ++ | 1.4 |
| S 863 | + | +++ | ++ | 1.2 |
| J 503 | + | ++ | +++ | 1.9 |
| J 507 | - | -- | +++ | 1.9 |
| J 517 | + | ++ | ++ | 1.3 |
| G 929 | ++ | ++ | ++ | 1.4 |
| G 932 | +++ | ++ | ++ | 1.4 |
| G 962 | +++ | ++ | ++ | 1.6 |
| G 965 | ++ | ++ | ++ | 1.5 |

US 8,025,880 B2

SEQUENCE LISTING

<160> NUMBER OF SEQ ID NOS: 29

<210> SEQ ID NO 1
<211> LENGTH: 17
<212> TYPE: DNA
<213> ORGANISM: Human

```
<400> SEQUENCE: 1
tacaggatcc acgcgta                                                17

<210> SEQ ID NO 2
<211> LENGTH: 19
<212> TYPE: DNA
<213> ORGANISM: Human

<400> SEQUENCE: 2
tgacaagctt gcggccgcg                                              19

<210> SEQ ID NO 3
<211> LENGTH: 15
<212> TYPE: DNA
<213> ORGANISM: Human

<400> SEQUENCE: 3
gaataggcca tggcg                                                  15

<210> SEQ ID NO 4
<211> LENGTH: 11
<212> TYPE: DNA
<213> ORGANISM: Human

<400> SEQUENCE: 4
cagtcaagct t                                                      11

<210> SEQ ID NO 5
<211> LENGTH: 64
<212> TYPE: DNA
<213> ORGANISM: Human

<400> SEQUENCE: 5
ttactcgcct ggccgtcgtg gcctttgttg gcctctcgct gggcgacatc cagatgaccc 60
agtc                                                              64

<210> SEQ ID NO 6
<211> LENGTH: 32
<212> TYPE: DNA
<213> ORGANISM: Human

<400> SEQUENCE: 6
agcgtacgta cgtttgattt ccaccttggt cc                               32

<210> SEQ ID NO 7
<211> LENGTH: 47
<212> TYPE: DNA
<213> ORGANISM: Human

<400> SEQUENCE: 7
gatgtctacg taggcctctc gctgggccag gtgcagctgg tccagtc               47

<210> SEQ ID NO 8
<211> LENGTH: 43
<212> TYPE: DNA
<213> ORGANISM: Human

<400> SEQUENCE: 8
accgatgggc ccttggtgga ggcggaggag acggcgacca ggg                   43

<210> SEQ ID NO 9
<211> LENGTH: 33
```

```
<212> TYPE: DNA
<213> ORGANISM: Human

<400> SEQUENCE: 9
tttgcatcga tcaggtgcag ctggtgcagt ctg                                   33

<210> SEQ ID NO 10
<211> LENGTH: 68
<212> TYPE: DNA
<213> ORGANISM: Human

<400> SEQUENCE: 10 acccccctcga gggatagatc ttcttctgag atcagctttt gttcagttcg tttgatttcc    60
accttggt                                                              68

<210> SEQ ID NO 11
<211> LENGTH: 71
<212> TYPE: DNA
<213> ORGANISM: Human

<400> SEQUENCE: 11 acccccctcga gttaggatag atcttcttct gagatcagct tttgttcagt tcgtttgatt    60
tccaccttgg t                                                          71

<210> SEQ ID NO 12
<211> LENGTH: 26
<212> TYPE: DNA
<213> ORGANISM: Human

<400> SEQUENCE: 12
atccaaaaag gagaaaaaac atgaaa                                          26

<210> SEQ ID NO 13
<211> LENGTH: 21
<212> TYPE: DNA
<213> ORGANISM: Human

<400> SEQUENCE: 13
gcttttagtt tccactttga g                                               21

<210> SEQ ID NO 14
<211> LENGTH: 20
<212> TYPE: DNA
<213> ORGANISM: Human

<400> SEQUENCE: 14
tgtgtgccac tagtgccagc                                                 20

<210> SEQ ID NO 15
<211> LENGTH: 18
<212> TYPE: DNA
<213> ORGANISM: Human

<400> SEQUENCE: 15
ttgctccaca taggcgca                                                   18

<210> SEQ ID NO 16
<211> LENGTH: 360
<212> TYPE: DNA
<213> ORGANISM: Human

<400> SEQUENCE: 16
caggtgcagc tggtgcagtc tggggaggc atcggacagc ctggagggtc cctgcgactc      60
```

```
gcctgtgaag cctctggatt cacattcaat ctctttgaga tggcctgggt ccgtcaggct    120
ccggggcaga gtctggaagt gatttcatac attggcagta gtggttctac aacgcgctac    180
gcagactccg tgaagggccg attcatcgtc tccagagaca cgacaagga gtcgatgttt    240 cttcagctca acagcctgag agtcgacgac acggccactt attttttgtgc agagattgaac   300 gggtgggccg ggtcaggatt agaccactgg ggccagggga ccctggtcgc cgtctcctcc    360
```

<210> SEQ ID NO 17
<211> LENGTH: 321
<212> TYPE: DNA
<213> ORGANISM: Human

<400> SEQUENCE: 17

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccttgtggac gttcggccaa    300
gggaccaagg tggaaatcaa a                                              321
```

<210> SEQ ID NO 18
<211> LENGTH: 120
<212> TYPE: PRT
<213> ORGANISM: Human

<400> SEQUENCE: 18

Gln Val Gln Leu Val Gln Ser Gly Gly Gly Ile Gly Gln Pro Gly Gly
1               5                   10                  15

Ser Leu Arg Leu Ala Cys Glu Ala Ser Gly Phe Thr Phe Asn Leu Phe
            20                  25                  30

Glu Met Ala Trp Val Arg Gln Ala Pro Gly Gln Ser Leu Glu Val Ile
        35                  40                  45

Ser Tyr Ile Gly Ser Ser Gly Ser Thr Thr Arg Tyr Ala Asp Ser Val
    50                  55                  60

Lys Gly Arg Phe Ile Val Ser Arg Asp Asn Asp Lys Glu Ser Met Phe
65                  70                  75                  80

Leu Gln Leu Asn Ser Leu Arg Val Asp Asp Thr Ala Thr Tyr Phe Cys
                85                  90                  95

Ala Arg Leu Asn Gly Trp Ala Gly Ser Gly Leu Asp His Trp Gly Gln
            100                 105                 110

Gly Thr Leu Val Ala Val Ser Ser
        115                 120

<210> SEQ ID NO 19
<211> LENGTH: 107
<212> TYPE: PRT
<213> ORGANISM: Human

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Trp
                85                  90                  95

Thr Phe Gly Gln Gly Thr Lys Val Glu Ile Lys
                100                 105

<210> SEQ ID NO 20
<211> LENGTH: 98
<212> TYPE: PRT
<213> ORGANISM: Human

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 21
<211> LENGTH: 120
<212> TYPE: PRT
<213> ORGANISM: Human

<400> SEQUENCE: 21

Gln Val Gln Leu Val Gln Ser Gly Gly Gly Ile Gly Gln Pro Gly Gly
1               5                   10                  15

Ser Leu Arg Leu Ala Cys Glu Ala Ser Gly Phe Thr Phe Asn Leu Phe
            20                  25                  30

Glu Met Ala Trp Val Arg Gln Ala Pro Gly Gln Gly Leu Glu Val Ile
        35                  40                  45

Ser Tyr Ile Gly Ser Ser Gly Ser Thr Thr Arg Tyr Ala Asp Ser Val
    50                  55                  60

Lys Gly Arg Phe Ile Val Ser Arg Asp Asn Asp Lys Glu Ser Met Phe
65                  70                  75                  80

Leu Gln Leu Asn Ser Leu Arg Val Asp Asp Thr Ala Thr Tyr Phe Cys
                85                  90                  95

Ala Arg Leu Asn Gly Trp Ala Gly Ser Gly Leu Asp His Trp Gly Gln
                100                 105                 110

Gly Thr Leu Val Ala Val Ser Ser
            115                 120

<210> SEQ ID NO 22
<211> LENGTH: 120
<212> TYPE: PRT
<213> ORGANISM: Human

<400> SEQUENCE: 22
```

Gln Val Gln Leu Val Gln Ser Gly Gly Ala Trp Gly Gln Pro Gly Ala
1               5                   10                  15

Ser Leu Arg Leu Ser Cys Glu Val Ser Gly Phe Pro Phe Asn Leu Tyr
                20                  25                  30

Glu Met Ile Trp Val Arg Gln Ala Pro Gly Lys Gly Leu Glu Trp Val
            35                  40                  45

Ala Tyr Ile Gly Ser Ser Gly Thr Leu Met Lys Tyr Ala Asp Ser Val
50                      55                  60

Lys Gly Arg Leu Thr Ile Ser Arg Asp Asn Ser Lys Asn Ser Leu Tyr
65                  70                  75                  80

Leu His Leu Asn Ser Pro Glu Val Glu Asp Thr Ala Ile Tyr Tyr Cys
                85                  90                  95

Ala Arg Phe Asn Gly Trp Ser Gly Ser Gly Leu Asp Tyr Trp Gly Gln
            100                 105                 110

Gly Thr Leu Val Ala Val Ser Ser
            115                 120

<210> SEQ ID NO 23
<211> LENGTH: 98
<212> TYPE: PRT
<213> ORGANISM: Human

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
50                      55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 24
<211> LENGTH: 124
<212> TYPE: PRT
<213> ORGANISM: Human

<400> SEQUENCE: 24

Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Asp Phe Lys Ala His
                20                  25                  30

Gly Met Ser Trp Val Arg Gln Ala Pro Gly Gln Gly Pro Glu Trp Met
            35                  40                  45

Gly Trp Ile Ser Gly Asn Asn Tyr Asn Thr Thr Tyr Ala Gln Ser Val
            50                  55                  60

Arg Gly Arg Val Thr Val Thr Thr Asp Thr Ser Thr Thr Thr Val Tyr
65                  70                  75                  80

Met Glu Leu Lys Asn Leu Arg Ser Asp Asp Thr Ala Val Tyr Phe Cys
                85                  90                  95

Ala Arg Asp Gln Gly Gly Ser Arg Phe Gly Glu Leu Leu Ile Leu Asp
            100                 105                 110

```
Tyr Trp Gly Gln Gly Thr Leu Val Thr Val Ser Ser
            115                 120

<210> SEQ ID NO 25
<211> LENGTH: 95
<212> TYPE: PRT
<213> ORGANISM: Human

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 26
<211> LENGTH: 107
<212> TYPE: PRT
<213> ORGANISM: Human

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Asn
            20                  25                  30

Leu Asn Trp Tyr Gln Gln Tyr Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Leu Leu
                85                  90                  95

Thr Phe Gly Gly Gly Thr Lys Val Asp Ile Lys
            100                 105

<210> SEQ ID NO 27
<211> LENGTH: 107
<212> TYPE: PRT
<213> ORGANISM: Human

<400> SEQUENCE: 27

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
                65                  70                  75                  80
Glu Asp Phe Ala Thr Tyr Tyr Cys Gln Gln Ser Tyr Ser Thr Pro Leu
                        85                  90                  95
Thr Phe Gly Gly Gly Thr Lys Val Glu Ile Lys
                100                 105

<210> SEQ ID NO 28
<211> LENGTH: 100
<212> TYPE: PRT
<213> ORGANISM: Human

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 29
<211> LENGTH: 112
<212> TYPE: PRT
<213> ORGANISM: Human

<400> SEQUENCE: 29

Asp Val Val Met Thr Gln Ser Pro Leu Ser Leu Pro Val Thr Leu Gly
1               5                   10                  15

Gln Ser Ala Ser Ile Ser Cys Arg Ser Ser Gln Gly Leu Val Tyr Leu
            20                  25                  30

Asp Gly Asn Thr Asn Leu Asn Trp Phe Arg Gln Arg Pro Gly Gln Ala
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Arg Val Glu Ile Lys
            100                 105                 110
```

IMMUNOGLOBULIN AGAINST HELICOBACTER PYLORI

CROSS-REFERENCE TO RELATED APPLICATIONS

This application claims priority from U.S. provisional application Ser. No. 60/904,241 filed Mar. 1, 2007.

FIELD OF THE INVENTION

The present invention relates to materials and methods for prevention, treatment and diagnosing of infections caused by *Helicobacter pylori* (*H. pylori*). More specifically the present invention relates to new specific variable antibody regions, derivatives thereof and the fully human immunoglobulin, Abba3, which exhibit specific activity to the BabA antigen, expressed by *H. pylori*, methods for the production of said immunoglobulins, their isolation and use, for example in detection of disease-causing *H. pylori*. The present invention also relates to immunization therapies, i.e. passive vaccination for the treatment and prevention of pathologic infections caused by *H. pylori* strains.

BACKGROUND OF THE INVENTION

*H. pylori* is a Gram negative bacterium that colonizes the human gastric mucosa causing chronic gastritis that may progress to peptic ulceration and gastric cancer (Blaser, M. J., and D. E. Berg. 2001. *Helicobacter pylori* genetic diversity and risk of human disease. J Clin Invest 107:767-773). *H. pylori* expresses adhesins on its surface which provides intimate adherence to the gastric mucosa, allowing these auxotroph organisms to gain nutrients from host tissues. The BabA adhesin is a member of the paralogous family of outer membrane proteins (Alm, R. A., J. Bina, B. M. Andrews, P. Doig, R. E. Hancock, and T. J. Trust. 2000. Comparative genomics of *Helicobacter pylori*: analysis of the outer membrane protein families. Infect Immun 68:4155-4168) that binds to fucosylated ABO/Lewis b blood group antigens which are expressed on epithelial cells (Boren, T., P. Falk, K. A. Roth, G. Larson, and S. Normark. 1993. Attachment of *Helicobacter pylori* to human gastric epithelium mediated by blood group antigens. Science 262:1892-1895 and Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-37).

BabA is a possible vaccine candidate since a high proportion of clinical isolates has been shown to express BabA (Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-377; Kim, S. Y., C. W. Woo, Y. M. Lee, B. R. Son, J. W. Kim, H. B. Chae, S. J. Youn, and S. M. Park. 2001. Genotyping CagA, VacA subtype, IceA1, and BabA of *Helicobacter pylori* isolates from Korean patients, and their association with gastroduodenal diseases. J Korean Med Sci 16:579-584, and Mizushima, T., T. Sugiyama, Y. Komatsu, J. Ishizuka, M. Kato, and M. Asaka. 2001. Clinical relevance of the babA2 genotype of *Helicobacter pylori* in Japanese clinical isolates. J Clin Microbiol 39:2463-2465). Active vaccination against *H. pylori* is difficult, due to the low immune activity in the GI-tract. One other issue is the high recombination rate of *H. pylori*. Passive immunization on the contrary is more advantageous, because the Abba3 antibodies bind to the antigen, making it difficult for the *H. pylori* to adhere to the mucosa.

Recent studies have also demonstrated a significant association between the expression of BabA and development of peptic ulcer and gastric cancer (Gerhard, M., N. Lehn, N. Neumayer, T. Boren, R. Rad, W. Schepp, S. Miehlke, M. Classen, and C. Prinz. 1999. Clinical relevance of the *Helicobacter pylori* gene for blood-group antigen-binding adhesin. Proc Natl Acad Sci USA 96:12778-12783 and Prinz, C., N. Hafsi, and P. Voland. 2003. *Helicobacter pylori* virulence factors and the host immune response: implications for therapeutic vaccination. Trends Microbiol 11:134-138). Currently, the feasibility of passive immunotherapy by delivery of highly ABO/Lewis b fucosylated glycoconjugates is being investigated (Gustafsson, A., A. Hultberg, R. Sjostrom, I. Kacskovics, M. E. Breimer, T. Boren, L. Hammarstrom, and J. Holgersson. 2006. Carbohydrate-dependent inhibition of *Helicobacter pylori* colonization using porcine milk. Glycobiology 16:1-10., and Xu, H. T., Y. F. Zhao, Z. X. Lian, B. L. Fan, Z. H. Zhao, S. Y. Yu, Y. P. Dai, L. L. Wang, H. L. Niu, N. Li, L. Hammarstrom, T. Boren, and R. Sjostrom. 2004. Effects of fucosylated milk of goat and mouse on *Helicobacter pylori* binding to Lewis b antigen. World J Gastroenterol 10:2063-2066). Alternatively, antibody derivatives that interfere with mucosal adherence could be administered orally or produced in situ by GRAS (Generally Recognised As Safe) microorganisms as shown by oral administration of IgG against *H. pylori* (Casswall, T. H., H. O, Nilsson, L. Bjorck, S. Sjostedt, L. Xu, C. K. Nord, T. Boren, T. Wadstrom, and L. Hammarstrom. 2002. Bovine anti-*Helicobacter pylori* antibodies for oral immunotherapy. Scand J Gastroenterol 37:1380-1385, and Keenan, J., S, Neal, R. Allardyce, and J. Roake. 2002. Serum-derived IgG1-mediated immune exclusion as a mechanism of protection against *H. pylori* infection. Vaccine 20:2981-2988), or by the administration of a *Lactobacillus* expressing a single-chain variable fragment (scFv) against *Streptococcus* mutants (Kruger, C., Y. Hu, Q. Pan, H. Marcotte, A. Hultberg, D. Delwar, P. J. Van Dalen, P. H. Pouwels, R. J. Leer, C. G. Kelly, C. van Dollenweerd, J. K. Ma, and L. Hammarstrom. 2002. In situ delivery of passive immunity by lactobacilli producing single-chain antibodies. Nat Biotechnol 20:702-706). scFv is a genetically engineered antibody that consists of the variable heavy chain (VH) and light chain (VL) of an immunoglobulin joined together by a flexible peptide linker.

The bacteria in the stomach are not only confronted by host-specific environmental conditions but also face changes of the mucosal glycosylation pattern during disease progression. The remarkable ability of *H. pylori* to establish a chronic and persistent infection despite is likely due to be due its extraordinarily high recombination rate (Falush, D., C. Kraft, N. S. Taylor, P. Correa, J. G. Fox, M. Achtman, and S. Suerbaum. 2001. Recombination and mutation during long-term gastric colonization by *Helicobacter pylori*: estimates of clock rates, recombination size, and minimal age. Proc Natl Acad Sci USA 98:15056-15061).

The ability of *H. pylori* to switch between tight adherence and non-adherence gives the bacterium access to nutrients leaking from the inflamed tissue but also exposes the bacterium to the inflammatory host response (Rhen, M., S. Eriksson, M. Clements, S. Bergstrom, and S. J. Normark. 2003. The basis of persistent bacterial infections. Trends Microbiol 11:80-86).

BabA contributes to the flexibility in binding by frameshift-based variation in the CT-rich leader-sequence, horizontal gene transfer and gene conversion with babB and babC (Aspholm-Hurtig, M., G. Dailide, M. Lahmann, A. Kalia, D. Ilver, N. Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa, M. G. Dominguez-Bello, G. I. Perez-Perez, M. J. Blaser, S, Normark, I. Carlstedt, S. Oscarson, S. Teneberg, D. E. Berg, and T. Boren. 2004. Functional adaptation of BabA, the *H. pylori* ABO blood group antigen binding adhesin. Science 305:519-522; Backstrom, A., C. Lundberg, D. Kersulyte, D. E. Berg, T. Boren, and A. Arnqvist. 2004. Metastability of *Helicobacter pylori* bab adhesin genes and dynamics in Lewis b antigen binding. Proc Natl Acad Sci USA 101:16923-16928 and Solnick, J. V., L. M. Hansen, N. R. Salama, J. K. Boonjakuakul, and M. Syvanen. 2004. Modification of *Helicobacter pylori* outer membrane protein expression during experimental infection of rhesus macaques. Proc Natl Acad Sci USA 101:2106-2111), outer membrane proteins (OMPs) closely related to BabA in their N- and C-terminal region but located in different loci. Even though BabA is mainly found in the babA locus, gene conversion with BabB located in the babB locus leads to the formation of either full a length BabA under the control of the weaker BabB promoter or to chimeric BabA/BabB genes with the site of recombination upstream of the unique region that distinguishes BabA from BabB (Colbeck, J. C., L. M. Hansen, J. M. Fong, and J. V. Solnick. 2006. Genotypic profile of the outer membrane proteins. BabA and BabB in clinical isolates of *Helicobacter pylori*. Infect Immun 74:4375-4378. 13. Dubel, S., F. Breitling, P. Fuchs, M. Braunagel, I. Klewinghaus, and M. Little. 1993. A family of vectors for surface display and production of antibodies. Gene 128:97-101). Recombination can also lead to the presence of BabB within the babA locus with subsequent loss of Lewis b binding in infected macaques and patients (Colbeck, J. C., L. M. Hansen, J. M. Fong, and J. V. Solnick. 2006. Genotypic profile of the outer membrane proteins BabA and BabB in clinical isolates of *Helicobacter pylori*. Infect Immun 74:4375-4378; Dubel, S., F. Breitling, P. Fuchs, M. Braunagel, I. Klewinghaus, and M. Little. 1993. A family of vectors for surface display and production of antibodies. Gene 128:97-101; Hennig, E. E., J. M. Allen, and T. L. Cover. 2006. Multiple chromosomal loci for the babA gene in *Helicobacter pylori*. Infect Immun 74:3046-3051; Hennig, E. E., R. Mernaugh, J. Edl, P. Cao, and T. L. Cover. 2004. Heterogeneity among *Helicobacter pylori* strains in expression of the outer membrane protein BabA. Infect Immun 72:3429-3435 and Solnick, J. V., L. M. Hansen, N. R. Salama, J. K. Boonjakuakul, and M. Syvanen. 2004. Modification of *Helicobacter pylori* outer membrane protein expression during experimental infection of rhesus macaques. Proc Natl Acad Sci USA 101:2106-2111). The third locus BabC, formerly only described in strain 26695, has recently been shown to be involved in the recombination exchange with BabA in additional strains (Colbeck, J. C., L. M. Hansen, J. M. Fong, and J. V. Solnick. 2006. Genotypic profile of the outer membrane proteins BabA and BabB in clinical isolates of *Helicobacter pylori*. Infect Immun 74:4375-4378. 13. Dubel, S., F. Breitling, P. Fuchs, M. Braunagel, I. Klewinghaus, and M. Little. 1993. A family of vectors for surface display and production of antibodies. Gene 128:97-101; Hennig, E. E., J. M. Allen, and T. L. Cover. 2006. Multiple chromosomal loci for the babA gene in *Helicobacter pylori*. Infect Immun 74:3046-3051. 21. Hennig, E. E., R. Mernaugh, J. Edl, P. Cao, and T. L. Cover. 2004. Heterogeneity among *Helicobacter pylori* strains in expression of the outer membrane protein BabA. Infect Immun 72:3429-3435).

Backström et al. (Backstrom, A., C. Lundberg, D. Kersulyte, D. E. Berg, T. Boren, and A. Arnqvist. 2004. Metastability of *Helicobacter pylori* bab adhesin genes and dynamics in Lewis b antigen binding. Proc Natl Acad Sci USA 101: 16923-16928) have shown that among clinical *H. pylori* isolates which had lost their ability to bind Lewis b, a small fraction of the bacterial population harbored a BabB/BabA chimera and Lewis b binding could be reconstituted by panning with Lewis b coated magnetic beads in vitro. This will enable the bacterium to respond to a changing glycosylation pattern upon an inflammatory host response. Gene conversion leads to the formation of a mosaic pattern of BabA, but mutation of the CBD (carbohydrate-binding domain) will lead to the loss of function and thereby to a reduced survival of *H. pylori* in the acute phase of infection in which the blood group antigens are still highly expressed on the epithelial cells.

The exclusive presence of babB in the babA locus of analyzed strains at the end of an experimental infection of rhesus macaques has led to the hypothesis that antigenic variation is used to avoid the host immune response (Solnick, J. V., L. M. Hansen, N. R. Salama, J. K. Boonjakuakul, and M. Syvanen. 2004. Modification of *Helicobacter pylori* outer membrane protein expression during experimental infection of rhesus macaques. Proc Natl Acad Sci USA 101:2106-2111). The antigenicity of *H. pylori* antigens in patient's sera has been tested in two reports but since the proteins were denatured with urea prior to 2D-separation, the possibility to detect conformational dependent membrane proteins was rather limited (Haas, G., G. Karaali, K. Ebermayer, W. G. Metzger, S. Lamer, U. Zimny-Arndt, S. Diescher, U. B. Goebel, K. Vogt, A. B. Roznowski, B. J. Wiedenmann, T. F. Meyer, T. Aebischer, and P. R. Jungblut. 2002. Immunoproteomics of *Helicobacter pylori* infection and relation to gastric disease. Proteomics 2:313-324 and Kimmel, B., A. Bosserhoff, R. Frank, R. Gross, W. Goebel, and D. Beier. 2000. Identification of immunodominant antigens from *Helicobacter pylori* and evaluation of their reactivities with sera from patients with different gastroduodenal pathologies. Infect Immun 68:915-920).

Polyclonal anti-BabA sera have been raised by immunization of rabbits with recombinant BabA isolated from inclusion bodies (Yamaoka, Y., J. Souchek, S. Odenbreit, R. Haas, A. Arnqvist, T. Boren, T. Kodama, M. S. Osato, O. Gutierrez, J. G. Kim, and D. Y. Graham. 2002. Discrimination between cases of duodenal ulcer and gastritis on the basis of putative virulence factors of *Helicobacter pylori*. J Clin Microbiol 40:2244-2246) and shown to recognize BabA in a majority of strains. To date, two monoclonal BabA specific scFvs have been described which were generated by immunization of rodents with a BabA-GST fusion protein, covering the BabA-J99 domain from amino acid 128 to 310 (Hennig, E. E., R. Mernaugh, J. Edl, P. Cao, and T. L. Cover. 2004. Heterogeneity among *Helicobacter pylori* strains in expression of the outer membrane protein BabA. Infect Immun 72:3429-3435). Only about half of the analyzed strains were positive by Westernblot analysis, probably due to the more restricted epitope of a monoclonal antibody in comparison to a polyclonal serum. In addition, the phage selection of the described scFv was performed on recombinant protein containing only a portion of BabA with no defined functional conformation.

A new approach in preventing infectious diseases transmitted through mucosal sites consists of the in situ delivery of antibody fragments by lactobacilli or other GRAS microorganisms (Kruger, C., Y. Hu, Q. Pan, H. Marcotte, A. Hultberg, D. Delwar, P. J. Van Dalen, P. H. Pouwels, R. J. Leer, C. G. Kelly, C. van Dollenweerd, J. K. Ma, and L. Hammarstrom.

2002. In situ delivery of passive immunity by lactobacilli producing single-chain antibodies. Nat Biotechnol 20:702-706).

The BabA adhesin has previously been identified and shown to be localized on the bacterial surface of *H. pylori* (SE 9602287-6). The blood group binding activity was shown to be pH dependent and the present inventors present evidence that the binding affinity to the Lewis-b receptor reveals a high equilibrium constant.

Intensive research has been directed to the immunological treatment and prevention of *H. pylori* induced infections. EP 0 484 148 (Ando & Nakamura) describes a method for treating and/or preventing upper gastrointestinal disease in mammals, said method comprising orally administering to a patient in need thereof an effective amount of a pharmaceutical composition comprising anti-*H. pylori* polyclonal immunoglobulins and a pharmaceutically acceptable carrier. The description further dwells on the combination of said treatment in combination with the administration of antibiotics. As the method of producing said polyclonal antibodies, EP 0 484 148 describes the isolation and purification of anti-*H. pylori* immunoglobulins from the sera and milk of mammals. *H. pylori* itself was not found in the stomachs of cows, goats, sheep, swine or horses, according to EP 0 484 148, but it was assumed that these animal species have colonizing microorganisms with antigenic determinants similar to those of *H. pylori* because they have immunoglobulins which cross-react to strains of *H. pylori* found in humans. Preferably, according to EP 0 484 148, large mammals, e.g. pregnant cows, are immunized with whole cells of *H. pylori* and the immunoglobulins subsequently extracted from the milk or colostrum. In the immunization experiments, NCTC Strain 11362 and clinical isolate *H. pylori* No. 153 were used to trigger the production of immunoglobulins. On the other hand, NCTC Strain 11637 was used for analyzing purposes. Immunization is claimed to yield an anti-*H. pylori* titer in the milk of such magnitude, that daily doses of 0.01-0.1 g/day immunoglobulin composition, are sufficient for successful therapy. The claimed interval of 0.01-0.1 g/day is however not supported by the experiments presented by Ando & Nakamura and so low doses have hitherto not proven efficient in clinical tests. The doses actually used in example 5 and 7 are in the order of magnitude of 1 g/day, i.e. 10-fold the upper limit of the given interval. Furthermore, it is very unlikely that unspecific immunoglobulin mixtures as those manufactured by Ando & Nakamura would be effective in claimed doses as similar doses are ineffective against other gastrointestinal pathogens. The simultaneous administration of antibiotics, extensively discussed in the description, underlines the insufficiency of the disclosed immunoglobulins.

EP 0 469 359 (Cordle & Schaller) likewise describes the immunization of mammals, preferably pregnant cows, with formalin killed *H. pylori* bacteria (ATCC Strain 26695). Anti-*H. pylori* polyclonal antibodies were isolated and purified from the milk and finally fed to piglets, in amounts of about 0.5 g immunoglobulins, three times daily. The results were assessed by determination of the number of biopsy specimens, which were positive for Gram-negative bacteria after the trial. Gram-negative bacteria were found in 78% of the piglets fed a non-immune nutrient but only (Sic!) in 35% of the piglets fed a nutrient containing so called specific anti-*H. pylori* antibodies.

US20040234529, a patent application of the same inventors as in the invention herein, discloses the BabA protein. Said adhesins and/or DNA are useful for diagnosis and therapy and/or prophylaxis directed against *H. pylori* induced infections, e.g. gastritis and acid peptic disease, i.e. active vaccination. They also disclose an immunoglobulin composition, which exhibits specific activity to a Lewis b antigen binding *Helicobacter pylori* adhesion for treatment and/or prevention of gastrointestinal diseases, caused by *H. pylori* for passive vaccination. Unlike the invention herein the antibody is an animal antibody and not a specific selected human antibody. Furthermore the applicants of the US20040234529 do not mention detection in fecal samples.

Even though the central part of BabA is most heterogeneous and determines the specificity of receptor binding (Aspholm-Hurtig, M., G. Dailide, M. Lahmann, A. Kalia, D. Ilver, N Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa, M. G. Dominguez-Bello, G. I. Perez-Perez, M. J. Blaser, S, Normark, I. Carlstedt, S. Oscarson, S. Teneberg, D. E. Berg, and T. Boren. 2004. Functional adaptation of BabA, the *H. pylori* ABO blood group antigen binding adhesin. Science 305:519-522 and Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-377), the yet unmapped carbohydrate-binding domain (CBD) cannot be subjected to a high rate of mutation without loss of function; nevertheless fine-tuning during evolution was shown by adaptation of BabA in *H. pylori* strains isolated from indigenous South American population that preferentially bind to O-Lewis b, which is the predominant blood group antigen in this continent (nominated as "Specialists" strains). Contrarily, strains isolated from continents in which the A/B Lewis b blood group antigens are more evenly represented in the host population demonstrate a more general binding capability against A/B Lewis b (including O-Lewis b) and were hence named "Generalist" binder (Aspholm-Hurtig, M., G. Dailide, M. Lahmann, A. Kalia, D. Ilver, N. Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa, M. G. Dominguez-Bello, G. I. Perez-Perez, M. J. Blaser, S, Normark, I. Carlstedt, S. Oscarson, S. Teneberg, D. E. Berg, and T. Boren. 2004. Functional adaptation of BabA, the *H. pylori* ABO blood group antigen binding adhesin. Science 305:519-522). The BabA sequences were aligned but no specific babA domains that would correspond to Generalist versus Specialists could be mapped. We therefore aimed to develop an antibody with specificity for the receptor-binding site and used the phage display technique to enrich for antibodies from patients whose sera featured competitive BabA binding characteristics towards Lewis b.

It is already known in the art how to produce human scFv-libraries derived from peripheral blood lymphocytes against various peptides. It is also known how to select for denaturated, linear, non-native peptides of *H. pylori*. But no previous documents describe the selection method, selecting for the native, non-denatured, three-dimensional BabA polypeptide.

Here, we present a human scFv-library derived from peripheral blood lymphocytes of *H. pylori* infected patients and one of the identified and selected BabA-specific human single chains was converted to a human IgG1 antibody, named Abba3. Abba3 scFv refers to the variable binding regions and includes derivatives thereof. Surprisingly the antibody binds to a majority of *H. pylori* clinical isolates and demonstrated similar binding characteristics as the A-Lewis b or B-Lewis b blood group sugar antigens, i.e. preferential recognition of the "Generalist" type of BabA, distributed most commonly world-wide. Abba3 antibodies neutralize the *H. pylori* by binding to BabA, making it difficult for the bacteria to adhere to the mucosa. Consequently the bacteria/antibody-complex disappears naturally from the GI-system. Since there is a low immunoactivity in the stomach-tract, antibody detection is less useful than antigen detection. Accordingly, a detection kit using Abba3 antibodies for detection of *H. pylori* in faecal samples are preferred. Because Abba3 is a fully human IgG1 antibody it has the advantage of being effective in the activation of complement-directed lysis of the bacteria, accordingly, also activating the immune system.

It is therefore an object of this invention to provide the antibody Abba3 selected for its ability to specifically bind to BabA of *H. pylori*, for use in passive vaccination. It is also an object of the invention to use Abba3 for antigen detection of *H. pylori* in faecal samples. Furthermore an object of this invention is to provide any antibody selected using the method described in the invention herein for its ability to specifically bind to BabA of *H. pylori*. Other objects and advantages will be more fully apparent from the following disclosure and appended claims.

SUMMARY OF THE INVENTION

Adherence to the human gastric mucosa by the pathogen *H. pylori* requires adhesins that belong to the *H. pylori* outer membrane (HOP) protein family. The best-characterized interaction is the one between the BabA adhesin and the fucosylated blood group ABO/Leb antigens that are expressed as glycoconjugates along the gastro-intestinal (GI) lining. Here, we describe the identification and selection of human scFv antibody fragments with specificity for the BabA protein, in particular a scFv clone that competes for binding with the Lewis b antigen (Leb). *H. pylori* infected patients whose serum demonstrated competitive binding activities with BabA-mediated bacterial binding to Leb were selected and RNA isolated from peripheral blood lymphocytes (PBLs) was used to construct a phage display scFv library. Purified native BabA adhesin from *H. pylori* was used to probe the library and a clone (Abba3) was identified, which was completed to a fully human IgG1 antibody and expressed in insect cells. Competitive binding with Leb and binding to a conformational dependent BabA immuno-epitope indicates a similar binding site as for the natural receptors, i.e. the ABH/Leb antigens. *H. pylori* strains with Generalist (ABO/Leb antigens) binding characteristics as described by Aspholm-Hurtig et al. 2004 were preferentially bound by the Abba3 antibody, suggesting structural and conformational differences in the generalist versus specialist type of BabA (Aspholm-Hurtig, M., G. Dailide, M. Lahmann, A. Kalia, D. Ilver, N. Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa M. G. Dominguez-Bello, G. I. Perez-Perez, M. J. Blaser, S, Normark, I. Carlstedt, S. Oscarson, S. Teneberg, D. E. Berg, and T. Boren. 2004).

We identified an Abba3 antibody that neutralizes the *H. pylori* by binding to BabA, making it difficult for the bacteria to colonize the mucosa, consequently Abba3/BabA-complex disappear naturally from the GI-tract. Abba3 is a fully human antibody that has the advantage of being non-immunogenic and the IgG1 isotype is effective in the activation of the immune effector functions. Abba3 scFv refers to the variable binding regions and includes derivatives thereof. Furthermore a detection kit using Abba3 antibodies and derivatives for detection of *H. pylori* in fecal samples is disclosed.

BRIEF DESCRIPTION OF THE DRAWINGS

FIG. 2 shows the sequence comparison of the deduced VH- (a) and VL- (b) amino acid sequences of the isolated BabA-binders with their closest human germline V-genes. (a) The high number of mutations of the VH-chains in comparison to their germline gene indicates affinity maturation. The VH sequence from clone 5 and 6 (SEQ ID NO: 21) differs from the Abba3 sequence (SEQ ID NO: 18) only in one amino acid exchange in the FR2 region. Dashes indicate sequence identity, and dots denote gaps in the sequence. (VH from clone C4 (SEQ ID NO: 22): IgHV3-48*3 (SEQ ID NO: 20) IgHD-19*01, IgHJ4*02; VH from clone C5 (SEQ ID NO: 24): IgHV1-18*01 (SEQ ID NO: 23), IgHD3-10*02, IgHJ4*02). Abba3-VL derived from germline-gene IgKV1-39*01 and J-segment IgKJ1*01. Clone 6 and clone C5 most likely derived from the same precursor as they originated from the same germline and J-segment (IgKJ4*01). VL- from clone 5 derived from the germline-gene IgKV2-30-1 by recombination with IgKJ1*01.

FIG. 10 is a table summarizing the binding analysis of the Abba3 antibody by means of ELISA and immunoblot. A distinct consistency can be noted between the ELISA and immunoblot binding towards the different strains. Column 5 indicates the ratio between Leb towards A-Leb binding according to Aspholm-Hurtig et al.; values higher then 2.5 were classified as Specialist binder and depicted in bold. The accession numbers of the BabA gene sequences from strains are listed in column 6.

DETAILED DESCRIPTION OF THE INVENTION AND PREFERRED EMBODIMENTS THEREOF

Selection of Donors Seropositive for BabA

Sera from 36 *H. pylori* infected Swedish patients were tested for their ability to inhibit binding of Leb multivalently attached to $^{125}$I-labelled albumin (Lebconjugate) to *H. pylori* strain 17875/Leb bacteria. Almost all patients demonstrated a low inhibitory titer (average of 1:50). However, six sera showed high titers of Leb inhibition (1:355 to 1:8361) and these were further tested for inhibition of Leb binding using two Swedish (Sw 7, Sw 44), one Peruvian (P 436), one Alaskan (A 714), one Spanish (S 863), one Chinese (Ch1) and one reference strain J99 (Alm, R. A., L. S. Ling, D. T. Moir, B. L. King, E. D. Brown, P. C. Doig, D. R. Smith, B. Noonan, B. C. Guild, B. L. deJonge, G. Carmel, P. J. Tummino, A. Caruso, M. Uria-Nickelsen, D. M. Mills, C. Ives, R. Gibson, D. Merberg, S. D. Mills, Q. Jiang, D. E. Taylor, G. F. Vovis, and T. J. Trust. 1999. Genomic-sequence comparison of two unrelated isolates of the human gastric pathogen *Helicobacter pylori*. Nature 397:176-180). Three of the sera showed high inhibition titers towards a majority of the strains (data not shown).

Generation of V-Gene Repertoires and scFv-Libraries

RNA from PBLs from the three patients with inhibition-positive sera was isolated and the corresponding cDNA was generated and used for amplification of genes encoding antibody V-regions. In order to avoid bias by preferential amplification of predominant clones, the VH- and VL-regions from each patient were amplified separately with family specific primers. The VL-kappa regions from each patient were pooled and cloned into the phagemid vector pSEX81 (Breitling, F., S. Dubel, T. Seehaus, I. Klewinghaus, and M. Little. 1991. A surface expression vector for antibody screening. Gene 104:147-153), resulting in three kappa VL-sublibraries each containing approximately $7\times10^5$ independent clones. Sequencing of 20 individual clones demonstrated complete diversity. Amplified VH-regions of each patient were cloned into the corresponding VL-kappa sublibrary, resulting in three separate scFv-libraries of approximately $7\times10^6$ individual clones each. In order to control the quality of the library, full length expression of the scFvpIII fusion protein was analyzed in a Western-blot by using a mAb against the pIII-domain (Tesar, M., C. Beckmann, P. Rottgen, B. Haase, U. Faude, and K. N. Timmis. 1995. Monoclonal antibody against pIII of filamentous phage: an immunological tool to study pIII fusion protein expression in phage display systems. Immunotechnology 1:53-64). Since 6 out of 15 individual clones expressed a scFv-pIII fusion protein, the actual size of the library was estimated to comprise $3\times106$ functional clones each.

Panning for Specific Binders

Figure 1:
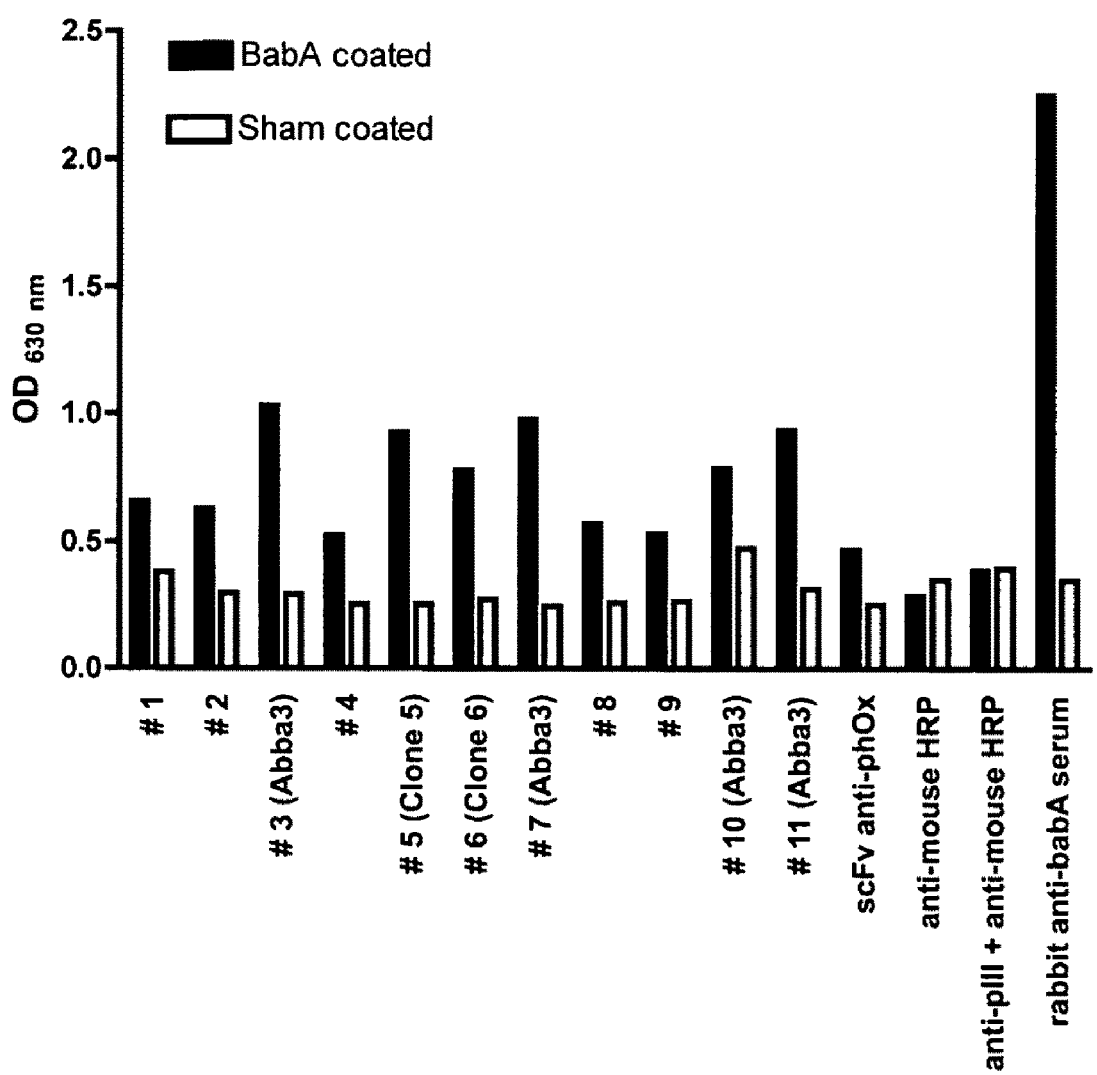
FIG. 1 shows scFv-pIII fusion proteins expressed by individual phagemid bearing clones which were analyzed for BabA binding in ELISA. Detection occurred with an anti-pIII mAb. Names in parenthesis were given to the clones after sequencing. As negative control, an irrelevant anti phOx scFv cloned in the same phagemid vector was equally detected.

Phage particles from a pool of the three libraries were produced by overinfection with helper-phage and subjected to three panning rounds on BabA coated immunotubes. In order to monitor an increase in BabA specific binders, the phages were also subjected to selection on BSA coated immunotubes. The enrichment factor, as measured by the ratio of phages eluted from BabA-coated immunotubes versus immunotubes only blocked with BSA, was shown to be 55 in the second panning round and 2381 in the third panning round. Single clones obtained after the third panning round were expressed as scFv-gIII fusion proteins and screened for BabA binding by ELISA. Of 24 clones analyzed, 14 revealed specific binding to BabA. FIG. 1 shows the screening ELISA assay of phagemid-expressed single clones.

Sequence analysis showed the occurrence and combination of similar V regions with the prevalence (6×) of one clone, hence named Abba3 (Anti-babA) (FIG. 2). Screening of the Abba3-VH region against the IMGT database revealed that it was generated by recombination of the germlinegene IgHV3-48*3 with the D-segment IgHD2-15*01 and the J-segment IgHJ4*03. VH-regions from other representative binders were derived from different B-cell precursors as they were derived from a different germline-gene or recombination occurred with different D- and J-segments (see legend FIG. 2). The Abba3 VL-chain was derived from the VL germline-gene IgGKV1D-39*01 by recombination with the J-segment IgKJ1*01. Similarly, the VL-regions from other binders were derived from different B-cell precursors as recombination occurred from different VL and J-segments.

Phages from the second panning-round were also panned on immobilized strain 17875/Leb and affinity eluted with the BabA ligand, i.e. Leb instead of regular triethylamine-buffer, resulting in an exclusive selection of Abba3 clones (data not shown).

Binding Specificity of Abba3

The predominant scFv Abba3 was subcloned in a prokaryotic expression vector, allowing detection with a monoclonal antibody against c-myc and IMAC-purification (Dubel, S., F.

Figure 3:
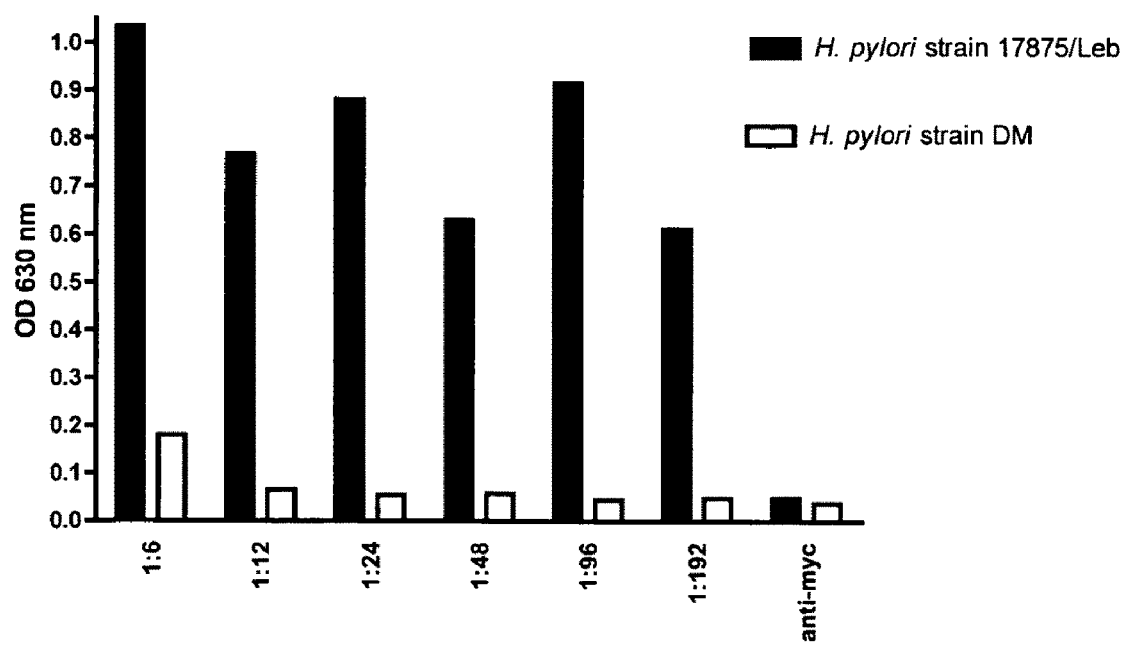
FIG. 3 shows scFv-Abba3 binding to *H. pylori* strain 17875/Leb but not to the corresponding strain babA1A2 mutant in which the BabA gene had been knocked out. IMAC-purified scFv-Abba 3 was serially diluted in PBS and incubated on ELISA wells coated with the corresponding strains. Binding was detected using an anti-myc tag mAb (9E10) and HRP-conjugated anti-mouse Ab.
Figure 4:
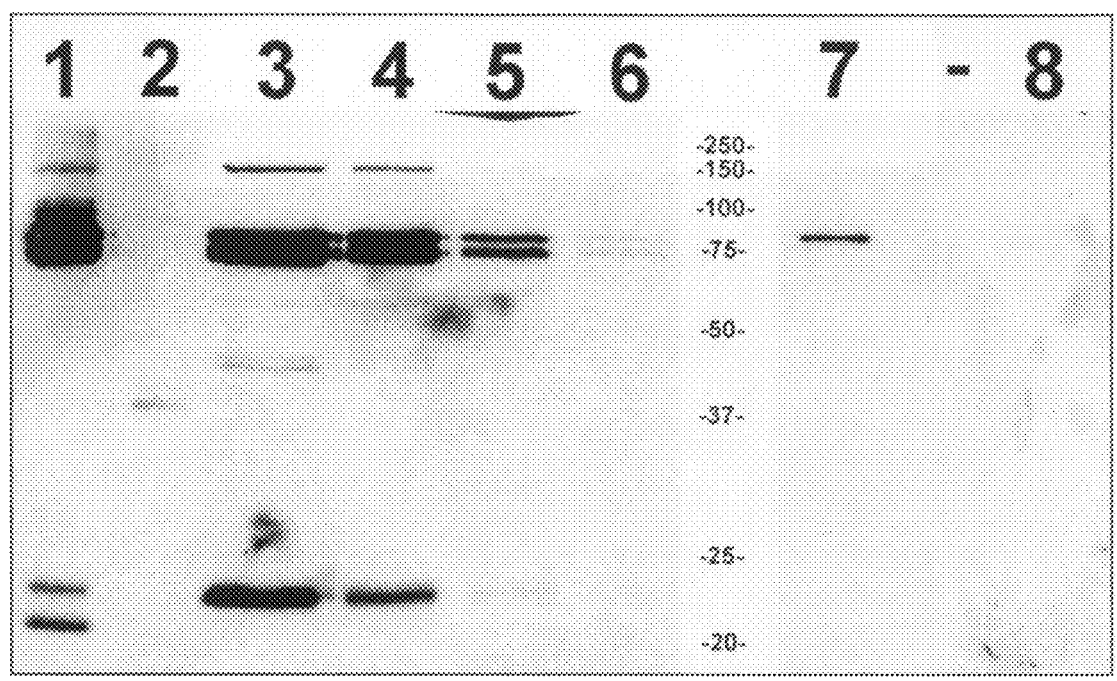
FIG. 4 shows ScFv-Abba3 recognizing BabA from *H. pylori* strain 17875/Leb lysate (Lane 1), but no band is visible with lysate of the BabA-double knock-out strain babA1A2 (Lane 2). BabA from strain 17875/Leb lysate is even recognized under harsh denaturing conditions (Lane 3 to 6). In contrast, purified BabA from strain 17875/Leb is recognized only if the protein is mildly treated (Lane 7) and the epitope is destroyed after addition of mercapto ethanol and heat treatment (Lane 8), suggesting stabilizing proteins in the bacterial lysate. Lane 1: non-reduced *H. pylori* lysate (5 µl of strain 17875/Leb, OD 1.0); Lane 2: non-reduced strain babA1A2, 5 µl of OD 1.0); Lane 3 to Lane 6: Harshly reduced *H. pylori* 17875/Leb lysate (12 µl, 5 µl, 1 µl, 0.2 µl resp. OD 1.0; 2.5% mercaptoethanol, 3% SDS and heating for 15 min at 96° C.) Lane 7: non-reduced, purified BabA from strain 17875/Leb (500 ng); Lane 8: reduced, purified BabA from strain 17875/Leb (500 ng).

Breitling, P. Fuchs, M. Braunagel, I. Klewinghaus, and M. Little. 1993. A family of vectors for surface display and production of antibodies. Gene 128:97-101 and Dubel, S., F. Breitling, I. Klewinghaus, and M. Little. 1992. Regulated secretion and purification of recombinant antibodies in *E. coli*. Cell Biophys 21:69-79). In order to test whether the scFv-Abba3 is able to recognize BabA on bacteria, an ELISA binding assay with immobilized *H. pylori* was performed. Serial dilution of the Abba3-scFv demonstrated binding to *H. pylori* strain 17875/Leb, but no binding to the corresponding negative control strain DM, in which the functional BabA gene (BabA2) as well as the nontranscribed BabA gene (BabA1) had been knocked out (Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-377) (FIG. 3). Immunoblot analysis further proved the specificity of Abba3-scFv as it recognized a band of the expected molecular weight in a bacterial lysate and purified protein from strain 17875/Leb (FIG. 4). Interestingly, the specific recognition occurred only if the purified BabA protein had been treated under mild conditions; treatment with a reducing agent and heating to 96° C. destroyed the epitope for Abba3 (FIG. 4, Lane 8) in analogy to described Lewis b binding characteristics (Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279: 373-377). This is in contrast to the recognition of BabA from *H. pylori* 17875/Leb lysates, where even harsh reducing and denaturing conditions did not abolish binding of the scFv in Western-blot. This could possibly be due to a complex formation between BabA and other stabilizing proteins, absent in the protein preparation after purification. The appearance of a double band in the bacterial lysate might be due to different glycosylation patterns as multiple N-glycoslylation sites (N—X—S/T) are located on the C-terminal region of BabA.

Figure 5:
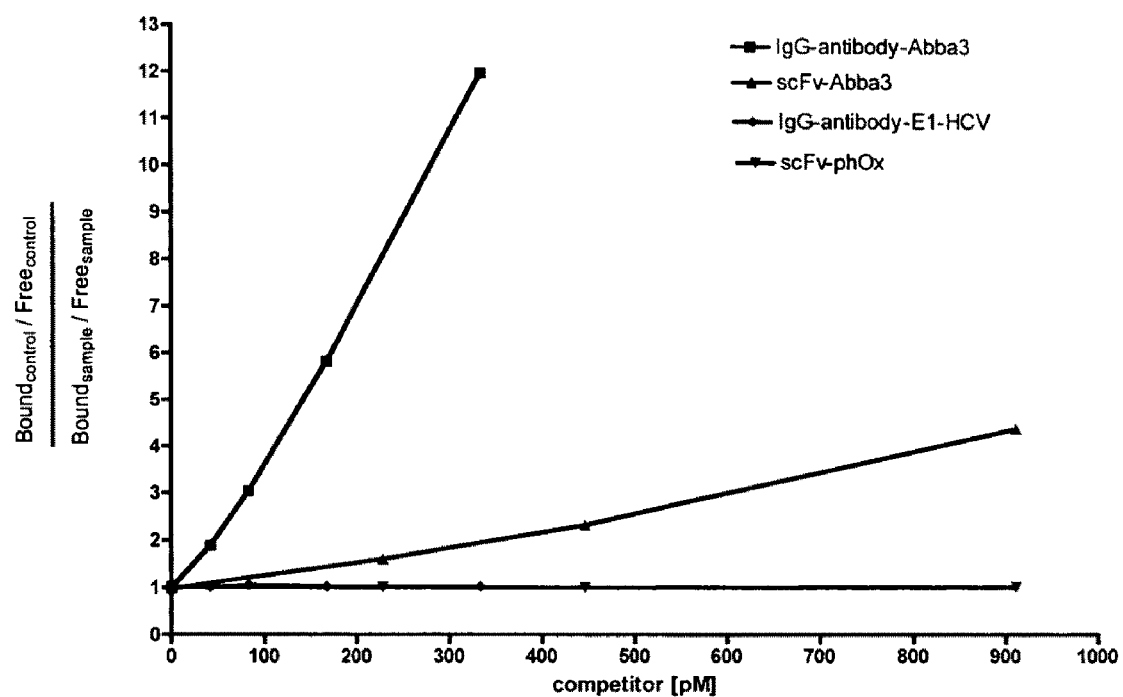
FIG. 5 shows the IgG-Abba3 and scFv derivative competing for binding on *H. pylori* with the BabA-receptor Leb. *H. pylori* strain 17875/Leb was incubated with a constant amount of radiolabeled HSA-Lewis b conjugate in the presence of various amounts of competitor. The relative affinity was expressed as the amount of competitor necessary for reducing binding of radioactive labelled Lewis b to *H. pylori* strain 17875/Leb to 50% (see text). The relative affinity of antibody Abba3 revealed to be five times higher (47 pM) then the scFv Abba3 (247 pM). The control antibody with specificity towards the E1-HCV envelope protein and a scFv with specificity towards the hapten 2-phenyloxazolone did not compete for Leb binding.
Figure 6:
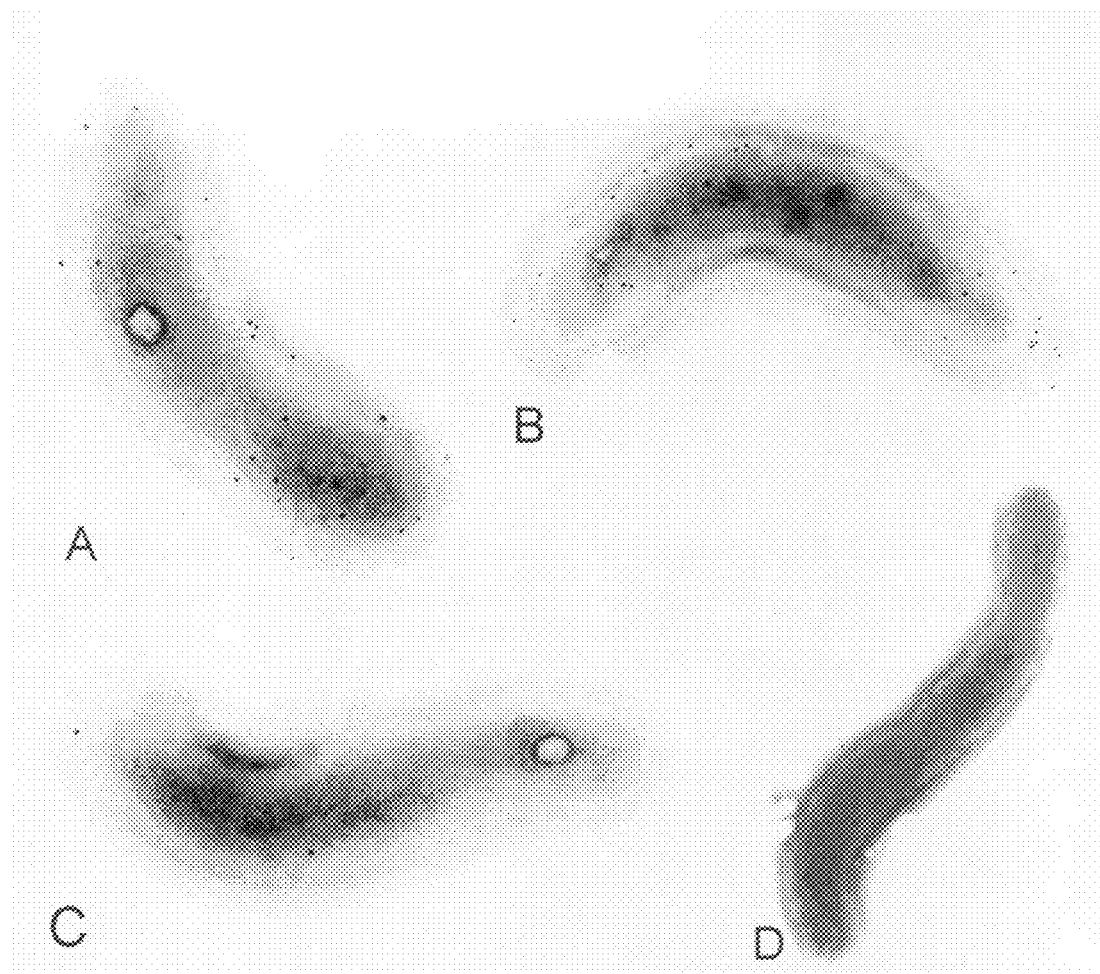
FIG. 6 shows the electron microscopy pictures demonstrating BabA-staining of *H. pylori* strain 17875/Leb by Abba3-Ab: bacteria were incubated with human antibodies and the bound fraction detected with gold labelled Protein A. Incubation of antibody Abba3-Ab with *H. pylori* strain 17875/Leb (A,B); antibody Abba3 with *H. pylori* strain DM (C), irrelevant antibody (anti-E1 HCV envelope) with *H. pylori* strain 17875/Leb (D).

In order to gain stability, avidity and superior ease in handling, the scFv was converted into a fully human IgG using an expression vector described elsewhere (Johansson, D. X., Drakenberg, J. K., Hopmann, K. H., Schmidt, A., Yari, F., Hinkula, J. and Persson M. A A. 2006. Efficient expression of recombinant human monoclonal antibodies in drosophila S2 cells. J Immunol Methods). The Abba3-antibody was produced in insect cells and showed unrestrained binding on bacteria coated on ELISA plates with no impairment upon multiple thawing cycles (data not shown). To test for competitive binding with Lewis b, the Abba3-scFv and the Abba3-antibody were serially diluted and incubated with *H. pylori* strain 17875/Leb in the presence of a constant amount of radioactively labelled Lewis b. The concentration of the scFv and IgG antibody, sufficient to reduce Lewis b binding to half of its maximum value, was determined to be 0.25 µM and 47 pM respectively. No inhibition of Lewis b binding was observed using an irrelevant scFv (directed against the hapten 2-phenyloxazolone) (Marks, J. D., H. R. Hoogenboom, T. P. Bonnert, J. McCafferty, A. D. Griffiths, and G. Winter. 1991. By-passing immunization. Human antibodies from V-gene libraries displayed on phage. J Mol Biol 222:581-597) or an irrelevant isotype matching human monoclonal antibody, which had been recombinantly produced (directed against the HCV envelope protein E1 (Johansson, D. X., K. Drakenberg, K. H. Hopmann, A. Schmidt, F. Yari, J. Hinkula, and M. A. Persson. 2007. Efficient expression of recombinant human monoclonal antibodies in *Drosophila* S2 cells. J Immunol Methods 318:37-46)) (FIG. 5). Staining of BabA on the bacterial outer membrane in electron microscopy could be demonstrated by incubation of the Abba3-antibody on *H. pylori* strain 17875/Leb, but not by incubation with the corresponding BabA knock out strain DM. As an additional negative control, the isotype matching human antibody did not reveal any staining on the BabA expressing *H. pylori* strain 17875/Leb (FIG. 6).

Reactivity Against *Helicobacter pylori* Isolates

Figure 7:
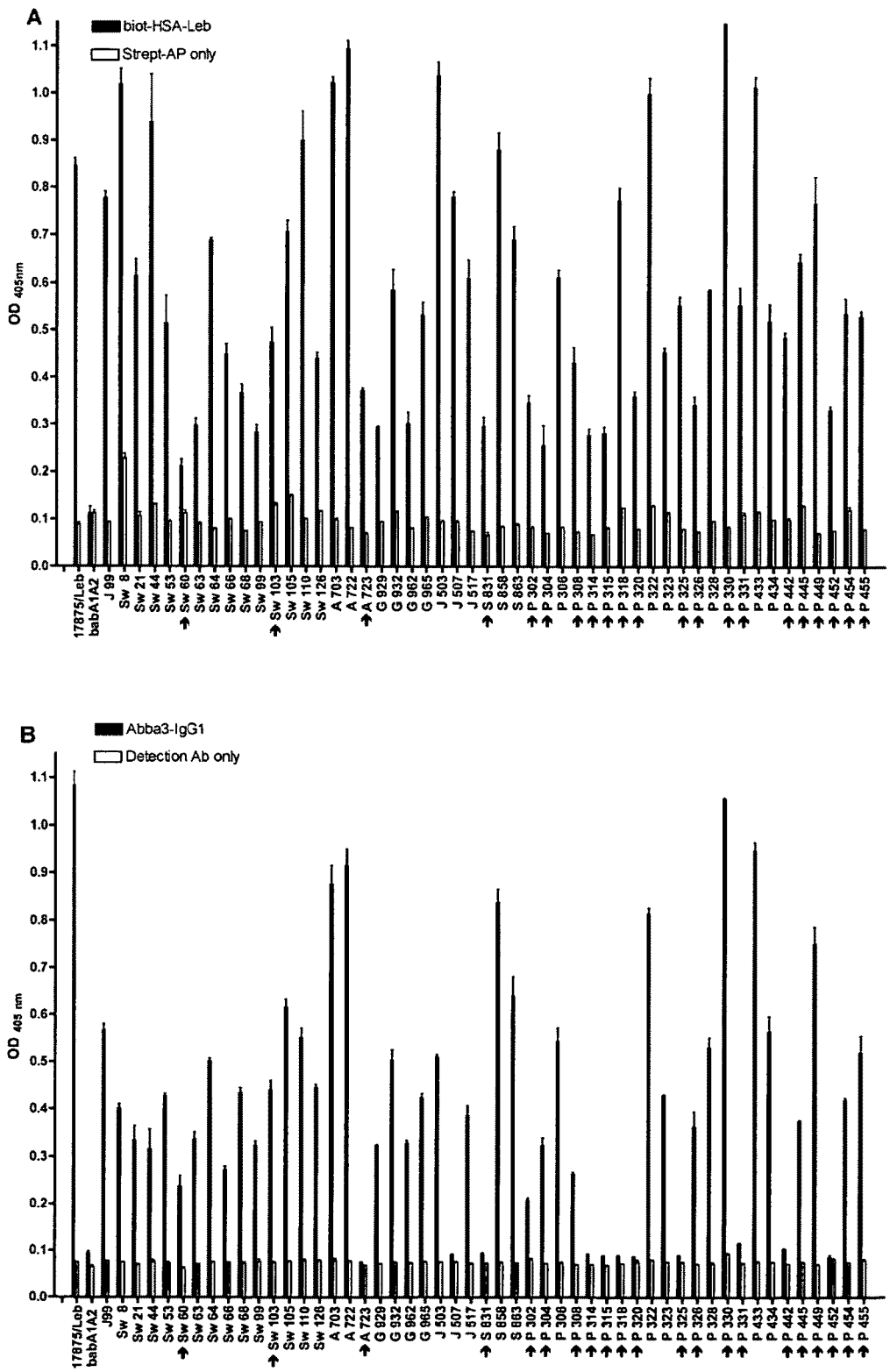
FIG. 7 shows the capacity of the Abba3-antibody for binding different *H. pylori* clinical isolates by ELISA (A). (A) Clinical *H. pylori* isolates were tested for functional BabA-expression in ELISA. Coated strains were probed with biotin-Leb conjugate and detected with AP-Streptavidin. (B) Using identical coating conditions, Abba3-IgG1 binding was tested by detection with an AP-conjugated anti-human. In total, 79% (41 out of 52) of analyzed strains were bound by Abba3-IgG. Specialists strains are marked with ↑
Figure 8:
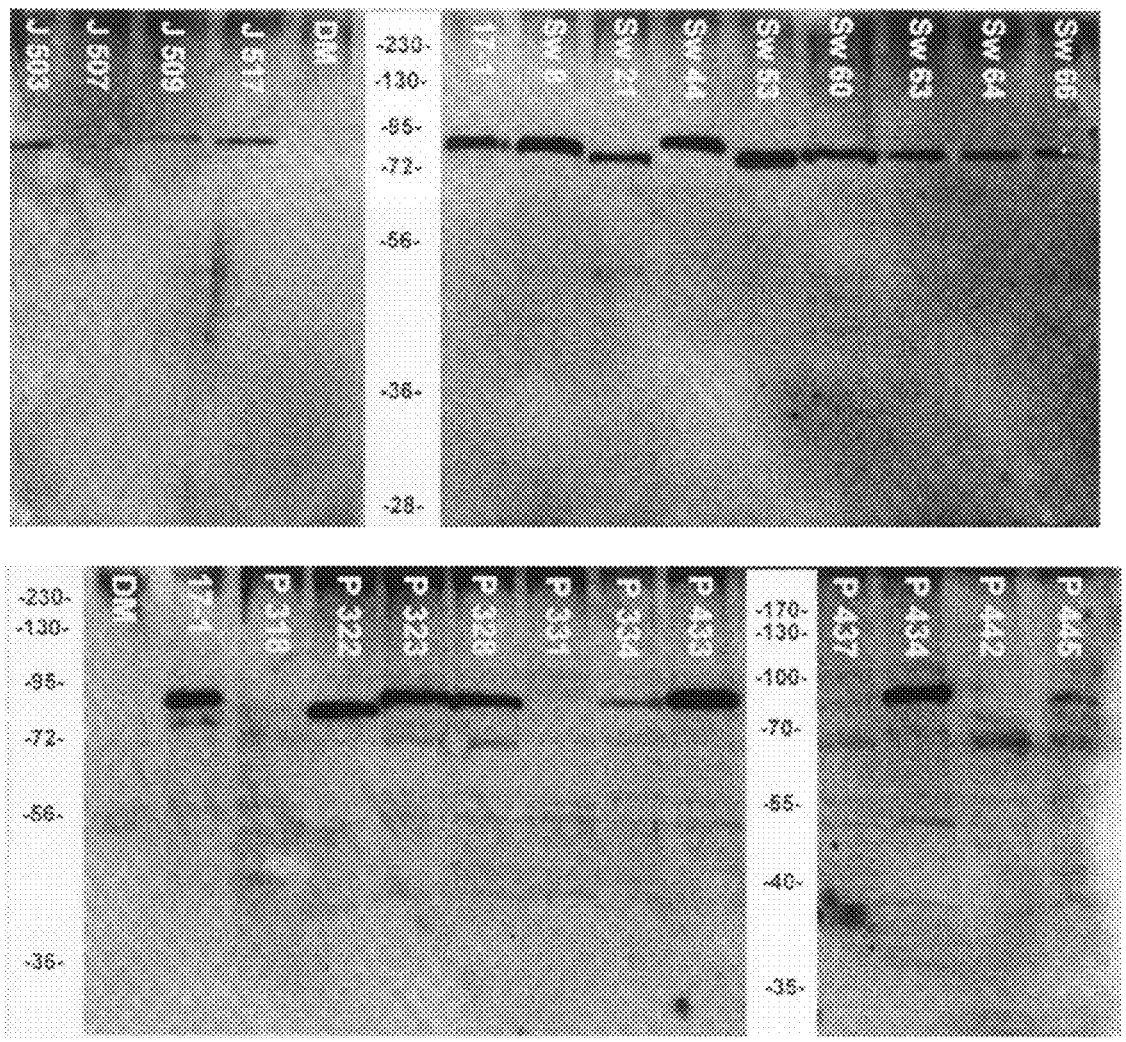
FIG. 8 shows the capacity of Abba3-antibody to recognize BabA from different *H. pylori* clinical isolates in immunoblot. *H. pylori* colonies from plates were scraped off, washed twice in PBS and normalized to an OD of 0.6. SDS-solubilized culture extracts were incubated at 37° C., separated by SDS-PAGE and transferred to a nitrocellulose membrane. Detection occurred with Abba3-IgG (6 µg/ml) followed by HRP-conjugated anti-human IgG. Two representative blots are shown.
Figure 9:
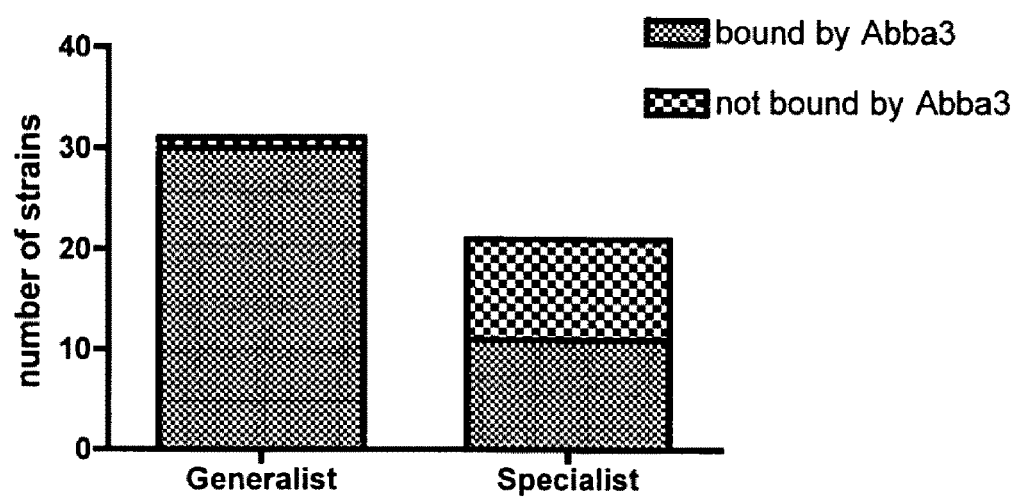
FIG. 9 is a graphical illustration of the ELISA and Western-blot binding data from FIG. 1: Nearly all strains with generalist Lewis b-binding characteristics were recognized by the Abba3 antibody (30 out of 31), whereas approximately only half (11 out of 21) of the strains with specialists Lewis b-binding characteristics were bound. Fisher's exact test reveals statistical significance with a confidence value of $p<0.0002$.

To test the prevalence of the Abba3 immuno epitope in BabA among clinical *H. pylori* strains worldwide, we performed a full series of ELISA and immunoblot tests with representative strains. For Abba3 analysis, only these *H. pylori* strains expressing a functional BabA protein were considered. We therefore tested strains for their capability to bind blood group antigen in an ELISA-binding assay (FIG. 7A). Using the same ELISA-conditions, the same strains were tested for Abba3 binding (FIG. 7B). Immunoblot analyses were performed by use of *H. pylori* whole cells extracts that had been treated according to the "mild protocol", i.e. without reducing conditions and by low temperature, before SDS-PAGE separation (Ilver, D., A. Arnqvist, J. Ogren, I. M. Frick, D. Kersulyte, E. T. Incecik D. E. Berg, A. Covacci, L. Engstrand, and T. Boren. 1998. *Helicobacter pylori* adhesin binding fucosylated histo-blood group antigens revealed by retagging. Science 279:373-377) (FIG. 8). Table 1 summarizes the binding characteristics of the clinical isolates used, i.e. binding capacity for the Leb ligand and for the Abba3-antibody. In addition, accession numbers of the corresponding babA genes are listed. The Abba3 antibody was found to recognize best BabA from *H. pylori* strains that bind the series of ABO/Leb antigens (defined as Generalists by Aspholm-Hurtig et al.) whereas the Abba3 antibody recognized BabA from specialist strains (specialists) less efficiently (FIG. 9). The majority of generalist strains (30 out of 31) were bound by the Abba3-Ab (the Japanese strain J 507 was the exception), whereas only 11 out of 21 specialists were recognized by the Abba3-Ab (Sw 60, Sw 103, P 302, P 304, P 308, P 326, P 330, P 445, P 449, P 454, P 455).

Preferential binding of the Abba3 antibody to Generalists in comparison to Specialists could be due to a part of the antibody reflecting the more bulky Gal and GalNAc end groups of the A-Lewis and B-Lewis blood group sugar antigens respectively. The higher binding prevalence of the Abba3 antibody compared to the antibody described in Hennig et al (Hennig, E. E., R. Mernaugh, J. Edl, P. Cao, and T. L. Cover. 2004. Heterogeneity among *Helicobacter pylori* strains in expression of the outer membrane protein BabA. Infect Immun 72:3429-3435) could be due to the receptor competitive binding characteristics and consequently the recognition of a more conserved epitope. We believe that the successful selection of a high affinity antibody was founded on the thorough screening of suitable patient sera with defined antibody binding characteristics.

Furthermore, phage selection was performed under conditions in which the immobilized antigen retained binding to its receptor, as verified by testing the binding of immobilized BabA with biotinylated Lewis b in immunotubes (data not shown). The application of phage display for exploiting and rescue of the immune repertoire from *H. pylori* infected patients proved to be successful in the selection of monoclonal antibodies with defined characteristics. Since the donors were all from Sweden it is likely that they had been infected by Generalists strains and even though the antibody variable regions are reshuffled for the construction of the phage display library, the likelihood for functional reassembly was apparently sufficient.

Since the immune activity is limited in the GI tract, passive form of immunization is preferred. The Abba3 antibodies bind to BabA, preventing the adherence of *H. pylori* to the gastric mucosa.

Occasionally there are complications associated with passive immunization when the antibodies derive from animals, due to allergic reactions. Since the Abba3 antibody is human the risk of side effects is reduced.

On account of the limited immune activity in the GI-tract, the possibility to diagnose *H. pylori* infection by detecting antibodies is restricted. For this reason the detection is preferred in feces samples.

A new approach in preventing infectious diseases transmitted through mucosal sites consists of the in situ delivery of antibody fragments by lactobacilli or other GRAS microorganisms (Kruger, C., Y. Hu, Q. Pan, H. Marcotte, A. Hultberg, D. Delwar, P. J. Van Dalen, P. H. Pouwels, R. J. Leer, C. G. Kelly, C. van Dollenweerd, J. K. Ma, and L. Hammarstrom. 2002. In situ delivery of passive immunity by lactobacilli producing single-chain antibodies. Nat Biotechnol 20:702-706). Accordingly, Abba3 and fragments thereof, with specificity against BabA may be used to prevent the colonization of *H. pylori* on the mucosa.

Furthermore, increasing evidence suggests the involvement of *H. pylori* in the pathogenesis of coronary artery disease (Kowalski, M., M. Pawlik, J. W. Konturek, and S. J. Konturek. 2006. *Helicobacter pylori* infection in coronary heart disease. J Physiolo Pharmacol 57:101-111). Compared to a non-human antibody, Abba3 antibody is of fully human origin that does not trigger an immunogenetic response and the IgG1 type has the advantage of being effective in the activation of complement-directed lysis of the bacteria, accordingly, activating effector functions of the immune system.

Example 1

Selection of Donors Positive for BabA-Antibodies

Sera from 36 *H. pylori* infected Swedish patients were tested for their ability to inhibit binding of radiolabeled Lewis b-HSA conjugate to the *H. pylori* strain CCUG17875 (17875/Leb). For easier recovery of a pellet, the bacterial strain 17875/Leb with an OD of 0.1 was diluted 1:60 with the bacterial strain 17874 which had lost its ability to bind Leb. Serial dilutions of the sera were diluted in blocking buffer (PBS 0.05% Tween 20, 1% BSA) and 50 µl of radioactively labelled Lewis b-HSA conjugate (0.01 ng/µl) were added to a final volume of 500 µl. After addition of 500 µl bacteria, tubes were softly mixed for 17 hours at RT (room temperature). Samples were centrifuged (13 000 g for 13 min) and the radioactivity of the pellet and supernatant was subsequently measured and put in relation to each other, representing the bound and free conjugate. The relative titer of the tested serum was the concentration sufficient to reduce the binding to half the maximum value as determined by binding of the conjugate in absence of any serum. Six of the sera with the highest titer were further tested for inhibition of radiolabeled Lewis b-antigen binding to seven *H. pylori* clinical isolates (Sw 7, Sw 44, P 436, A 714, S 863, Ch1 (described here) and J99 (Alm, R. A., L. S. Ling, D. T. Moir, B. L. King, E. D. Brown, P. C. Doig, D. R. Smith, B. Noonan, B. C. Guild, B. L. deJonge, G. Carmel, P. J. Tummino, A. Caruso, M. Uria-Nickelsen, D. M. Mills, C. Ives, R. Gibson, D. Merberg, S. D. Mills, Q. Jiang, D. E. Taylor, G. F. Vovis, and T. J. Trust. 1999. Genomic-sequence comparison of two unrelated isolates of the human gastric pathogen *Helicobacter pylori*. Nature 397: 176-180).

Example 2 cDNA Synthesis and PCR Amplification of Human Variable Regions

Peripheral blood mononuclear cells (PBMCs) from 10 ml patient's blood were isolated on a Ficoll-gradient and total RNA was extracted using standard protocols (Qiagen, Hilden, Germany). First-strand cDNA was synthesized with an oligo-d(T) primer (Amersham Biosciences, Buckingham, UK) and human variable immunoglobulin genes were PCR-amplified in 50 µl reactions containing 1 µl of the cDNA, 200 µM dNTPs, 5 µl of 10× reaction buffer, 1 U of polymerase (BD-Advantage2, BD Biosciences Clontech, Palo Alto, Calif.) and the appropriate family-based sense and antisense primers (500 nM) with 36 cycles (15 seconds denaturation at 94° C., 30 seconds annealing at 65° C., 30 seconds at 72° C.). The sense and antisense primer have been described elsewhere (Marks, J. D., H. R. Hoogenboom, T. P. Bonnert, J. McCafferty, A. D. Griffiths, and G. Winter. 1991. By-passing immunization. Human antibodies from V-gene libraries displayed on phage. J Mol Biol 222:581-597 and Welschof, M., P. Terness, F. Kolbinger, M. Zewe, S. Dubel, H. Dorsam, C. Hain, M. Finger, M. Jung, G. Moldenhauer, and et al. 1995. Amino acid sequence based PCR primers for amplification of rearranged human heavy and light chain immunoglobulin variable region genes. J Immunol Methods 179:203-214). For the variable kappa light-chain amplification the sense primer was extended at the 5' end by the sequence TACAGGATCCACGCGTA (SEQ ID NO:1) in order to introduce a Mlu I cloning site and the antisense primer by TGACAAGCTTGCGGCCGCG (SEQ ID NO:2) for introduction of a Not I site; for variable heavy-chain amplification the sense primer was extended by the sequence GAATAG-GCCATGGCG (Nco I) (SEQ ID NO:3) and the antisense primer by the sequence CAGTCAAGCTT (Hind III site) (SEQ ID NO:4). The antisense primers anneal at the 5' end of the CH1 and Constant Kappa region respectively. All amplifications were performed independently for each of the family specific sense primers. The PCR-products were pooled, gel-extracted (Qiagen) and digested with Mlu I/Not I (New England Biolabs) for variable light-chains and Nco I/Hind III for cloning of variable heavy-chains. After digestion, fragments were gel-purified again and stored at −20° C.

Example 3

Construction of a scFv-Library

The phagemid vector pSEX81-phOx (Breitling, F., S. Dubel, T. Seehaus, I. Klewinghaus, and M. Little. 1991. A surface expression vector for antibody screening. Gene 104: 147-153) was digested with Mlu I/Not I in the presence of calf intestinal phosphatase (CIP) and separated in a 0.7% agarose gel and extracted (Qiagen, Germany). 100 ng of the digested vector was ligated with 10 ng of the purified variable light chains in a final volume of 40 µl with 1 U ligase (Roche) at 16° C. overnight. Plasmid DNA was ethanol precipitated, electroporated in *E. coli* strain XL1-blue (Stratagene), and bacteria were grown for 1 h in 1 ml SOCmedia (LB containing 0.1 M glucose) to allow recuperation. Bacteria were subsequently plated on SOBGAT plates (0.1 M glucose, 100 µg/ml ampicillin, 12.5 µg/ml tetracycline), and incubated overnight at 37° C. Clones were scraped off and vector DNA isolated with anion exchange chromatography columns (Macherey & Nagel, Germany). For cloning of the variable heavy chains, vector DNA was digested with Hind III/Nco I (New England Biolabs), ligated with the appropriately digested VH-chains, transformed in XL-1 blue and grown as described above. Independent clones were scraped off and stored in 25% glycerine at −80° C., representing the final scFv-library.

Example 4

Phage-Display Selection

Phage-associated antibodies were retrieved from the libraries essentially as described by Schier et al. 1996 (Schier, R., J. Bye, G. Apell, A. McCall, G. P. Adams, M. Malmqvist, L. M. Weiner, and J. D. Marks. 1996. Isolation of high-affinity monomeric human anti-c-erbB-2 single chain Fv using affinity-driven selection. J Mol Biol 255:28-43). Panning was performed in Maxisorb Immunotubes (Nunc, Wiebaden, Germany) coated overnight with 5 µg purified BabA (Department of Oral Biology, Umeå University, Sweden) at 4° C. and blocked with 2% MPBS (PBS containing 2% (w/v)) low fat dried skimmed milk. Tubes coated with BSA were used as negative controls. For selection, phages (1012 colony-forming units) were blocked by the addition of an equal volume of PBS containing 4% milk (w/v), added to the tubes and incubated under constant rolling for 2 h at room temperature (RT). The solution was subsequently discarded and the tubes were washed 10 times with PBS in the first panning round. With progressing panning rounds, washing stringency was increased by vortexing 10 times with PBS/0.1% Tween 20. Bound phages were eluted by addition of 1 ml triethylamine (0.1 M) for 5 min with gentle agitation and neutralization with 0.5 ml Tris-HCl, pH 7.4 (1 M). The neutralized mixture was used to infect 20 ml of exponential-phase *Escherichia coli* XL1-blue grown in 2YT (12.5 µg/ml tetracycline) at 37° C. After incubation for 15 min at 37° C. without shaking, bacteria were shaken for 45 min, plated on SOBGAT-Plates (see above), and incubated overnight at 37° C. The bacteria were harvested as described and the production of phages for the subsequent panning round was performed by inoculation of 10 ml LB-media (Ampicillin 100 µg/ml, 0.1 M glucose) with an OD of 0.4. The titer of eluted phages containing helper phage- or phagemid-genome were determined by titration of the cfu on LB-Kanamycin (70 µg/ml)— or LBAmpicillin (100 µg/ml)—plates respectively, essentially as described by Koch et al. 2000 (Koch, J., F. Breitling, and S. Dubel. 2000. Rapid titration of multiple samples of filamentous bacteriophage (M13) on nitrocellulose filters. Biotechniques 29:1196-1198, 2002). The enrichment of specific binders during the selection procedure was determined by dividing the number of phages eluted from BabA-coated immunotubes by the number of phages eluted from BSA-coated immunotubes.

Example 5

ELISA-Screening with scFv-gIII Fusion Proteins

BabA specific scFvs were screened by taking advantage of the expressed pIII-protein encoded in the phagemid vector, modified but essentially as described by Mersmann et al. 1998 (Mersmann, M., A. Schmidt, M. Tesar, A. Schoneberg, M. Welschof, S. Kipriyanov, P. Terness, M. Little, K. Pfizenmaier, and D. Moosmayer. 1998. Monitoring of scFv selected by phage display using detection of scFvpIII fusion proteins in a microtiter scale assay. J Immunol Methods 220:51-58). Briefly, production of scFv-gIII fusion proteins in logarithmic grown bacteria was induced by IPTG (100 µM) for 16 h at 30° C. Bacteria were centrifuged and the pellet was incubated in spheroblast solution (50 mM Tris-HCl pH 8.0, 20% sucrose, 1 mM EDTA) for 20 min on ice, followed by centrifugation at 20 000 g for 45 mM at 4° C. The supernatant, representing the periplasmic extract was diluted with the same volume of 4% MPBS) and used in an ELISA assay. ELISA wells (Nunc Microtitre plates, Germany) were coated with 200 ng of BabA over night at 4° C. in coating buffer (Na2CO3-NaHCO3 pH 9.6). After blocking with 2% MPBS, the periplasmic extract was added and incubated for 4 h at RT. Antigen-bound scFv-pIII fusion protein was detected by incubation with a mouse monoclonal antibody specific for pIII (Tesar, M., C. Beckmann, P. Rottgen, B. Haase, U. Faude, and K. N. Timmis. 1995. Monoclonal antibody against pIII of filamentous phage: an immunological tool to study pIII fusion protein expression in phage display systems. Immunotechnology 1:53-64); MobiTec, Germany) for 1 h at RT, followed by a horseradish peroxidase-conjugated rabbit anti-mouse antibody (Dako, Denmark) for 1 h at RT. Colorization was done with TMB-(3,3',5,5'-Tetramethylbenzidin, Merck-Germany) in substrate buffer (100 mM Sodium-acetate/Citric acid pH 4.9/H2O2 0.004%). As a negative binding control, a 2-phenyloxazolone (anti-phOx) (Marks, J. D., H. R. Hoogenboom, T. P. Bonnert, J. McCafferty, A. D. Griffiths, and G. Winter. 1991. By-passing immunization. Human antibodies from V-gene libraries displayed on phage. J Mol Biol 222: 581-597) scFv was expressed in the same phagemid vector and expression of this scFv was analyzed using ELISA coated, phOx-conjugated BSA.

Example 6

Subcloning into the Prokaryotic Expression Vector pOPE101

The entire scFv expression cassette from the phagemid vector pSEX81 was subcloned into the prokaryotic expression vector pOPE101 (Genbank #Y14585) at the Nco I and Not I sites. (The clone is named pOPE101-Abba3 and was deposited under the Budapest treaty at DSMZ-Deutsche Sammlung von Mikroorganismen and Zellkulturen GmbH, in Braunschweig Germany. It received deposit number DSM19101 and deposit date 28 Feb. 2007). The C-terminal myc- and (His)6-Tag allows detection and IMAC purification respectively. Purification from the periplasmic space was performed as described by Breitling et al. 2001 (Breitling, F., Moosmayer, D., Brocks, B., Dubel, S. 2001. Construction of scFv from hybridoma by two-step cloning. Antibody Engineering ISDN 3-540-41354-5:41-55).

Example 7

Immuno-Blot

For quality control of the scFv-library, 10 µl of the periplasmic extract from IPTG-induced single colonized bacteria was separated on a 12% SDSNuPage Bis-Tris gel (Invitrogen, CA). Separated proteins were transferred to a Immobilon PVDF-membrane (Millipore, Bredford, Mass.), blocked with 2% MPBS (PBS containing 2% low fat dried skimmed milk) and visualized with an anti-gIII mAb (MobiTec, Gottingen, Germany), followed by an AP-conjugated rabbit anti-mouse (Fab)2 Ab (Sigma-Aldrich, Germany) and substrate. For functional binding analyses, BabA or variable amounts of Helicobacter pylori bacteria, resuspended and adjusted in PBS to an OD of 0.6, were either solubilized in one volume SDS-sample buffer (62 mM Tris-HCl pH 6.8, 25% glycerol, 2% SDS, bromphenolblue) and heated to 37° C. for 10 minutes (according to Ilver et al. 1998 (Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-377)) or resuspended in 1 vol. SDS-sample buffer containing mercaptoethanol (5%) (or additionally 3% SDS) and heated to 96° C. Samples were subjected to SDS-PAGE and separated proteins were transferred onto a Hybond-ECL nitrocellulose membrane (Amersham Biosciences). The membrane was blocked with 2% M-PBS and IMAC-purified scFv-Abba3 (diluted in PBS) or Abba3-Ab (6 µg/ml in T-PBS 0.05%) was added over night at 4° C. Detection of bound scFv was performed by incubation of the membrane with a biotinylated murine anti-myc mAb 9E10, followed by Streptavidin-HRP-conjugate. Bound Abba3-antibodies were detected by incubation with an HRP-conjugated anti-human IgG Ab (Dako, Denmark), diluted 1:3000 in T-PBS 0.05%. After each antibody incubation step, the membrane was washed 4 times with T-PBS 0.05%. Visualization was performed with ECL plus Western Blotting Detection system kit (Amersham Biosciences) according to the manufacturer's protocol.

Example 8

Production of a Complete Human Antibody

Variable regions were cloned into the insect cell expression vector pMThIgG1-V carrying the constant regions of the human IgG1 heavy chain and human kappa chain respectively (Johansson, D. X., Drakenberg, J. K., Hopmann, K. H., Schmidt, A., Yari, F., Hinkula, J. and Persson M. A A. 2006. Efficient expression of recombinant human monoclonal antibodies in *drosophila* S2 cells. J Immunol Methods). PCR amplification was performed using primer for the VL chain:

```
VL 5' SfiI,
                                          (SEQ ID NO:5)
TTACTCGCCTGGCCGTCGTGGCCTTTGTTGGCCTCTCGCTGGGCGACATC

CAGATGACCCAGTC;

VL 3' BsiWI,
                                          (SEQ ID NO:6)
AGCGTACGTACGTTTGATTTCCACCTTGGTCC;

and for the VH chain:

VH 5' SnaBI,
                                          (SEQ ID NO:7)
GATGTCTACGTAGGCCTCTCGCTGGGCCAGGTGCAGCTGGTCCAGTC;

VH 3' ApaI,
                                          (SEQ ID NO:8)
ACCGATGGGCCCTTGGTGGAGGCGGAGGAGACGGCGACCAGGG;
```

PCR amplification was performed using 100 ng of the phagemid vector as a template, 25 pmol each of the VL and VH primer pair respectively, 2 µM MgCl2, 0.2 mM dNTP and 10 U of Taq polymerase (Promega). After an initial denaturation step at 94° C. for 2 min, 32 cycles were performed as followed: 15 sec 94° C., 30 sec 62° C., 30 sec 72° C.; one final elongation step was performed for 5 min at 72° C. PCR products were purified with Qiagen PCR purification kit (Hilden, Germany) and digested with the appropriate restriction enzymes prior to cloning. A stable antibody secreting S2 cell line (Invitrogen, USA) was established as previously described and antibodies in the media were purified and enriched using protein G columns (Amersham Pharmacia, Uppsala, Sweden). Purity and functionality of the purified antibody was analyzed by Coomassie staining and ELISA respectively.

Example 9

Production of *Lactobacillus* Expressing Antibody Fragments

The scFv-encoding gene derived from the variable regions (VH and VL) of the Abba3 antibody was amplified by PCR using the primer: 5'ClaI-ABBA3 (TTTGCATCGATCAGGT-GCAGCTGGTGCAGTCTG) (SEQ ID NO:9); as a sense primer and Vk-mycXhoI (ACCCCCTCGAGGGATA-GATCTTCTTCTGAGATCAGCTTTTGT-TCAGTTCGTTTGAT TTCCACCTTGGT) (SEQ ID NO:10); or Vk-myc-STOP-XhoI (ACCCCCTCGAGTTAG-GATAGATCTTCTTCTGAGAT-CAGCTTTTGTTCAGTTCGTT TGATTTCCACCTTGGT) (SEQ ID NO:11); as an antisense primer for cloning into the vector pLP502-1 and pLP502-2 respectively. These shuttle vectors allow cloning and propagation in *Escherichia coli* and expression in *Lactobacillus* since they contain both an *E. coli* and *Lactobacillus* origin of replication and *Lactobacillus* specific regulatory sequences and promoter upstream of their cloning site. In vector pLP502-1, the scFv expression cassette was cloned as a fusion to the *Lactobacillus* membrane-protein gene prtp, mediating the expression of the scFv cassette on the cell-surface. Vector pLP502-2 allows the secretion of the scFv outside the bacterial cell due to the presence of a termination signal after the scFv sequence. ScFv expression was analyzed either by immunoblotting or by a soluble ELISA assay of *Lactobacillus casei* (ATCC 293) transformed strains using a monoclonal antibody against the co-expressed myc-tag and an AP-conjugated anti-mouse antibody for detection.

Example 10

Production and Use of an Oral Vaccine Using the Modified *Lactobacillus*

The modified *lactobacillus* strain of Example 9 is grown, harvested and freeze-dried as known in the industry and then filled into standard hard gelatine capsules at an amount in the range of at least $10^4$ to $10^7$ CFU per gram. Such capsules are given for a week to a group of patients known to be infected by *H. pylori*. After this period are the patients reanalyzed for *H. pylori* infection using standard methods or the method described herein, and the infection is shown to have been eliminated or reduced in several patients.

Example 11

ELISA-Binding on *Helicobacter pylori* Strains

Antibody-Abba3 was tested for its capacity to bind clinical isolates of *H. pylori*. Strains were grown for 40-45 hours on *Brucella* agar medium supplemented with 10% bovine blood and 1% IsoVitox (Svenska LABFAB, Ljusne, Sweden) at 37° C., under 10% CO2 and 5% O2. Bacteria were scraped off and washed twice by suspension in PBS, centrifugation at 4000 g and resuspension of the pellet in PBS. Optical density was adjusted to an OD600 nm of 0.6 and 100 µl was used to coat individual wells of a 96 well Maxisorb ELISA plate (Nunc, Denmark). After over-night incubation at 4° C., the plates were blocked with 2% M-PBS and antibody diluted in T-PBS (PBS 0.05% Tween20) was added over night at 4° C. Detection of the antibody was performed by incubation of an AP-conjugated anti-human IgG (Dako, Denmark) for 1 hour at RT followed by the addition of 4-Nitrophenyl phosphate at 1 mg/ml (Sigma-Aldrich, Germany). Absorbance was read at 405 nm after 40 min of color development. For the Lewis-b-binding assay, biotinylated HSA Lewis-b glycoconjugate (Isosep. Tullinge, Sweden) was added (0.115 µg/ml, over night at 4° C.) into the wells of an *H. pylori* coated ELISA plate. Bound glycoconjugate was detected by incubation with a 1:2000 dilution of AP-conjugated Streptavidin for 45 min at RT. The wells were washed 4 times with T-PBS 0.05% and color absorption at 405 nm was subsequently measured 10 minutes after addition of 1 mg/ml 4-Nitrophenyl phosphate (Sigma-Aldrich, Germany).

Example 12

Nucleotide Sequence Analysis of BabA

Strains were grown as described above and colonies were scraped off the plates and washed and resuspended in PBS to an optical density of OD 1. One ml of this suspension was used to isolate genomic DNA according to the manufacturer's instructions (Qiagen, Germany). BabA fragments covering the first nucleotide to approximately nucleotide 1200 were amplified by PCR using 4 µl of the genomic bacterial DNA as a template and a combination of either one of the forward primer babA2-271 (Aspholm-Hurtig, M., G. Dailide, M. Lahmann, A. Kalia, D. Ilver, N. Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa, M. G. Dominguez-Bello, G. I. Perez-Perez, M. J. Blaser, S, Normark, I. Carlstedt, S. Oscarson, S. Teneberg, D. E. Berg, and T. Boren. 2004. Functional adaptation of BabA, the *H. pylori* ABO blood group antigen binding adhesin. Science 305:519-522) (5'-ATCCAAAAAGGAGAAAAAACAT-GAAA-3') (SEQ ID NO:12)/babA2-Leader (5'-GCTTT-TAGTTTCCACTTTGAG-3') (SEQ ID NO:13) with one of the backward primer J11R (5"-TGTGTGCCACTAGTGC-CAGC-3') (SEQ ID NO:14) or A26R (5'-TTGCTCCACAT-AGGCGCA-3') (SEQ ID NO:15). The PCR fragments were ligated into a T-vector and sequenced with T7 and SP6 promoter specific primers.

Example 13

Sequencing and DNA Analysis

Nucleotide sequences were determined by the dideoxy chain-termination method of Sanger using the Big Dye Terminator Cycle Sequencing kit (Applied Biosystems, Foster City, Calif.) or using the services of MWG-Biotech AG, Ebersberg, Germany. IgG-germline sequences of human V-D-J segments were determined using the IMGT company online services. Assembly and sequence analysis was performed with the Vector NTI 10 program (Invitrogen, CA).

Example 14

Pre-Immunoelectron Microscopy (p-iEM)

*H. pylori* strain 17875/Leb and DM (BabA2 and BabA double knock out) were grown as described above, scraped off the plates and resuspended and adjusted in PBS to an OD600 nm of 1. An aliquot of each strain was resuspended in 2% bovine serum albumin (BSA fraction V) in 0.1 M sodiumcacodylate buffer (caco) for 15 min. The bacteria were then centrifuged and resuspended with the primary human antibody Abba3 or an irrelevant human anti-Hepatitis C virus antibody (HCV) of the same isotype, diluted (1+1) in 0.1 M caco+0.1% BSA and incubated for 60 min. After incubation, the bacteria were washed twice in 0.1 M caco+0.1% BSA and resuspended in the same buffer containing protein A conjugated to 10 nm goldparticles (Amersham, England) and incubated for 45 min. Adding glutaraldehyde to a final concentration of 1% terminated the incubation. The samples were fixed over night at 4° C. Bacteria were subsequently centrifuged to a pellet and embedded for conventional electron microscopy as described elsewhere (Gross, N. T., K. Hultenby, S. Mengarelli, P. Camner, and C. Jarstrand. 2000. Lipid peroxidation by alveolar macrophages challenged with *Cryptococcus neoformans, Candida albicans* or *Aspergillus fumigatus*. Med Mycol 38:443-449) and examined in a Tecnai 10 transmission electron microscope (Fei, The Netherlands) at 80 kV and digital images were collected by a Megaview III camera (AnalySiS, Münster, Germany).

Example 15

Direct-Immunoelectron Microscopy (d-iEM)

Before embedding, small aliquots of the pellet were taken and resuspended in distilled water. Small drops (3 µl) were placed on formvar coated grids and allowed to attach for 5 minutes. Excess water was removed by a filter paper and the grids were air dried for 5 minutes and examined in a Tecnai 10 electron microscope at 100 kV and images were recorded on photographic films.

Example 16

Immunoassay for In Vitro Diagnostic Use for Detection of *H. pylori* or BabA

For in vitro diagnostic use, Abba3 can be used as an enzyme immunoassay for the quantitative determination of *H. pylori* or BabA as one of the virulence factors in stool samples. For the test, *H. pylori* is captured in a sandwich-type method by specific antibodies: Polyclonal anti-Helicobacter serum are immobilized in the wells of a microwell plate and after blocking and a wash step with PBS as known in the art, a suspension of the stool sample to be examined and controls are pipetted at ambient temperature for incubation. Detection of bound bacteria occurs by addition of the enzyme (e.g. peroxidase)-conjugated Abba3 antibody in the microwell plate at room temperature followed by further washing steps and color formation upon addition of substrate. The extinction is proportional to the concentration of *H. pylori* present in the sample.

Example 17

Production of a Test Kit

Kits using immunoassay technique, which relies on the specific binding action between an antigen and a corresponding antibody, for example Abba3, has proven to be a reliable method for determining the presence (or absence) of a pathogen in a specimen. In this case *H. pylori* in a feacal sample.

A class of devices known as immunochromatographic test (ICT) devices uses the immunoassay technique in combination with a label that is conjugated with the antibody and is now commonly used for rapid, reliable field tests to determine the presence or absence of a particular analyte. The label, when attached to antibody/antigen molecules that are then amassed together in a specific, restricted area, becomes readily detectable by the naked human eye, or by a scanning device, depending on the type of label used. In general, the label can be a particle of latex, gold, or carbon, a radioactive particle, a magnetic particle, or have other physical or chemical properties that allow it to be fixed or attracted to a certain defined area. ICT devices that use the sandwich technique are particularly easy to use. With this technique, labeled antibody that binds with the specific antigen to be assayed is mixed with the sample that is suspected of containing the specific antigen. If the antigen is present in the sample, the labeled antibody binds with the antigen to form a label-antibody-antigen complex. A second antibody that is immovably fixed at a test zone and that also binds with the specific antigen binds the label-antibody-antigen complex at the test zone. A positive result is made visible by the accumulation of the label at the test zone. Such devices are standard products, readily available, economical and can be used by unskilled workers.

Example 18

Sequences of AbbaVH and Abba VL

Attached hereto is a sequence list showing the nucleotide sequences of AbbaVH (SEQ ID NO:16) and Abba VL (SEQ ID NO:17), and the amino acid sequences of AbbaVH (SEQ ID NO:18) and Abba VL (SEQ ID NO:19).

REFERENCES

1. Achtman, M., T. Azuma, D. E. Berg, Y. Ito, G. Morelli, Z. J. Pan, S. Suerbaum, S. A. Thompson, A. van der Ende, and L. J. van Doorn. 1999. Recombination and clonal groupings within *Helicobacter pylori* from different geographical regions. Mol Microbiol 32:459-470.
2. Alm, R. A., J. Bina, B. M. Andrews, P. Doig, R. E. Hancock, and T. J. Trust. 2000. Comparative genomics of *Helicobacter pylori*: analysis of the outer membrane protein families. Infect Immun 68:4155-4168.
3. Alm, R. A., L. S. Ling, D. T. Moir, B. L. King, E. D. Brown, P. C. Doig, D. R. Smith, B. Noonan, B. C. Guild, B. L. deJonge, G. Carmel, P. J. Tummino, A. Caruso, M. Uria-Nickelsen, D. M. Mills, C. Ives, R. Gibson, D. Merberg, S. D. Mills, Q. Jiang, D. E. Taylor, G. F. Vovis, and T. J. Trust. 1999. Genomic-sequence comparison of two unrelated isolates of the human gastric pathogen *Helicobacter pylori*. Nature 397:176-180.
4. Aspholm-Hurtig, M., G. Dailide, M. Lahmann, A. Kalia, D. Ilver, N. Roche, S. Vikstrom, R. Sjostrom, S. Linden, A. Backstrom, C. Lundberg, A. Arnqvist, J. Mandavi, U. J. Nilsson, B. Velapatino, R. H. Gilman, M. Gerhard, T. Alarcon, M. Lopez-Brea, T. Nakazawa, J. G. Fox, P. Correa, M. G. Dominguez-Bello, G. I. Perez-Perez, M. J. Blaser, S, Normark, I. Carlstedt, S. Oscarson, S. Teneberg, D. E. Berg, and T. Boren. 2004. Functional adaptation of BabA, the *H. pylori* ABO blood group antigen binding adhesin. Science 305:519-522.
5. Backstrom, A., C. Lundberg, D. Kersulyte, D. E. Berg, T. Boren, and A. Arnqvist. 2004. Metastability of *Helicobacter pylori* bab adhesin genes and dynamics in Lewis b antigen binding. Proc Natl Acad Sci USA 101:16923-16928.
6. Blaser, M. J., and D. E. Berg. 2001. *Helicobacter pylori* genetic diversity and risk of human disease. J Clin Invest 107:767-773.
7. Boren, T., P. Falk, K. A. Roth, G. Larson, and S. Normark. 1993. Attachment of *Helicobacter pylori* to human gastric epithelium mediated by blood group antigens. Science 262:1892-1895.
8. Breitling, F., S. Dubel, T. Seehaus, I. Klewinghaus, and M. Little. 1991. A surface expression vector for antibody screening. Gene 104:147-153.
9. Breitling, F., Moosmayer, D., Brocks, B., Dubel, S. 2001. Construction of scFv from hybridoma by two-step cloning. Antibody Engineering ISDN 3-540-41354-5:41-55.
10. Cao, J., Y. Sun, T. Berglindh, B. Mellgard, Z. Li, B. Mardh, and S. Mardh. 2000. *Helicobacter pylori*-antigen-binding fragments expressed on the filamentous M13 phage prevent bacterial growth. Biochim Biophys Acta 1474:107-113.
11. Casswall, T. H., H. O, Nilsson, L. Bjorck, S. Sjostedt, L. Xu, C. K. Nord, T. Boren, T. Wadstrom, and L. Hammarstrom. 2002. Bovine anti-*Helicobacter pylori* antibodies for oral immunotherapy. Scand J Gastroenterol 37:1380-1385.
12. Colbeck, J. C., L. M. Hansen, J. M. Fong, and J. V. Solnick. 2006. Genotypic profile of the outer membrane proteins BabA and BabB in clinical isolates of *Helicobacter pylori*. Infect Immun 74:4375-4378.
13. Dubel, S., F. Breitling, P. Fuchs, M. Braunagel, I. Klewinghaus, and M. Little. 1993. A family of vectors for surface display and production of antibodies. Gene 128:97-101.
14. Dubel, S., F. Breitling, I. Klewinghaus, and M. Little. 1992. Regulated secretion and purification of recombinant antibodies in *E. coli*. Cell Biophys 21:69-79.
15. Falush, D., C. Kraft, N. S. Taylor, P. Correa, J. G. Fox, M. Achtman, and S. Suerbaum. 2001. Recombination and mutation during long-term gastric colonization by *Helicobacter pylori*: estimates of clock rates, recombination size, and minimal age. Proc Natl Acad Sci USA 98:15056-15061.
16. Gerhard, M., N. Lehn, N. Neumayer, T. Boren, R. Rad, W. Schepp, S. Miehlke, M. Classen, and C. Prinz. 1999. Clinical relevance of the *Helicobacter pylori* gene for blood-group antigen-binding adhesin. Proc Natl Acad Sci USA 96:12778-12783.
17. Gross, N. T., K. Hultenby, S. Mengarelli, P. Camner, and C. Jarstrand. 2000. Lipid peroxidation by alveolar macrophages challenged with *Cryptococcus neoformans*, *Candida albicans* or *Aspergillus fumigatus*. Med Mycol 38:443-449.
18. Gustafsson, A., A. Hultberg, R. Sjostrom, I. Kacskovics, M. E. Breimer, T. Boren, L. Hammarstrom, and J. Holgersson. 2006. Carbohydratedependent inhibition of *Helicobacter pylori* colonization using porcine milk. Glycobiology 16:1-10.
19. Haas, G., G. Karaali, K. Ebermayer, W. G. Metzger, S. Lamer, U. Zimny-Arndt, S. Diescher, U. B. Goebel, K. Vogt, A. B. Roznowski, B. J. Wiedenmann, T. F. Meyer, T. Aebischer, and P. R. Jungblut. 2002. Immunoproteomics of *Helicobacter pylori* infection and relation to gastric disease. Proteomics 2:313-324.
20. Hennig, E. E., J. M. Allen, and T. L. Cover. 2006. Multiple chromosomal loci for the babA gene in *Helicobacter pylori*. Infect Immun 74:3046-3051.

21. Hennig, E. E., R. Mernaugh, J. Edl, P. Cao, and T. L. Cover. 2004. Heterogeneity among *Helicobacter pylori* strains in expression of the outer membrane protein BabA. Infect Immun 72:3429-3435.
22. Ilver, D., A. Arnqvist, J. Ogren, I. M. Frick, D. Kersulyte, E. T. Incecik, D. E. Berg, A. Covacci, L. Engstrand, and T. Boren. 1998. *Helicobacter pylori* adhesin binding fucosylated histo-blood group antigens revealed by retagging. Science 279:373-377.
23. Johansson, D. X., K. Drakenberg, K. H. Hopmann, A. Schmidt, F. Yari, J. Hinkula, and M. A. Persson. 2007. Efficient expression of recombinant human monoclonal antibodies in *Drosophila* S2 cells. J Immunol Methods 318:37-46.
24. Johansson, D. X., Drakenberg, J. K., Hopmann, K. H., Schmidt, A., Yari, F., Hinkula, J. and Persson M. A A. 2006. Efficient expression of recombinant human monoclonal antibodies in *drosophila* S2 cells. J Immunol Methods.
25. Keenan, J., S, Neal, R. Allardyce, and J. Roake. 2002. Serum-derived IgG1-mediated immune exclusion as a mechanism of protection against *H. pylori* infection. Vaccine 20:2981-2988.
26. Kim, S. Y., C. W. Woo, Y. M. Lee, B. R. Son, J. W. Kim, H. B. Chae, S. J. Youn, and S. M. Park. 2001. Genotyping CagA, VacA subtype, IceA1, and BabA of *Helicobacter pylori* isolates from Korean patients, and their association with gastroduodenal diseases. J Korean Med Sci 16:579-584.
27. Kimmel, B., A. Bosserhoff, It Frank, R. Gross, W. Goebel, and D. Beier. 2000. Identification of immunodominant antigens from *Helicobacter pylori* and evaluation of their reactivities with sera from patients with different gastroduodenal pathologies. Infect Immun 68:915-920.
28. Koch, J., F. Breitling, and S. Dubel. 2000. Rapid titration of multiple samples of filamentous bacteriophage (M13) on nitrocellulose filters. Biotechniques 29:1196-1198, 2002.
29. Kowalski, M., M. Pawlik, J. W. Konturek, and S. J. Konturek. 2006. *Helicobacter pylori* infection in coronary heart disease. J Physiolo Pharmacol 57:101-111.
30. Kruger, C., Y. Hu, Q. Pan, H. Marcotte, A. Hultberg, D. Delwar, P. J. van Dalen, P. H. Pouwels, R. J. Leer, C. G. Kelly, C. van Dollenweerd, J. K. Ma, and L. Hammarstrom. 2002. In situ delivery of passive immunity by lactobacilli producing single-chain antibodies. Nat Biotechnol 20:702-706.
31. Marks, J. D., H. R. Hoogenboom, T. P. Bonnert, J. McCafferty, A. D. Griffiths, and G. Winter. 1991. By-passing immunization. Human antibodies from V-gene libraries displayed on phage. J Mol Biol 222:581-597.
32. Mersmann, M., A. Schmidt, M. Tesar, A. Schoneberg, M. Welschof, S. Kipriyanov, P. Terness, M. Little, K. Pfizenmaier, and D. Moosmayer. 1998. Monitoring of scFv selected by phage display using detection of scFvpIII fusion proteins in a microtiter scale assay. J Immunol Methods 220:51-58.
33. Mizushima, T., T. Sugiyama, Y. Komatsu, J. Ishizuka, M. Kato, and M. Asaka. 2001. Clinical relevance of the babA2 genotype of *Helicobacter pylori* in Japanese clinical isolates. J Clin Microbiol 39:2463-2465.
34. Peck, B., M. Ortkamp, K. D. Diehl, E. Hundt, and B. Knapp. 1999. Conservation, localization and expression of HopZ, a protein involved in adhesion of *Helicobacter pylori*. Nucleic Acids Res 27:3325-3333.
35. Pride, D. T., R. J. Meinersmann, and M. J. Blaser. 2001. Allelic Variation within *Helicobacter pylori* babA and babB. Infect Immun 69:1160-1171.
36. Prinz, C., N. Hafsi, and P. Voland. 2003. *Helicobacter pylori* virulence factors and the host immune response: implications for therapeutic vaccination. Trends Microbiol 11:134-138.
37. Rhen, M., S. Eriksson, M. Clements, S. Bergstrom, and S. J. Normark. 2003. The basis of persistent bacterial infections. Trends Microbiol 11:80-86.
38. Rondot, S., J. Koch, F. Breitling, and S. Dubel. 2001. A helper phage to improve single-chain antibody presentation in phage display. Nat Biotechnol 19:75-78.
39. Schier, R., J. Bye, G. Apell, A. McCall, G. P. Adams, M. Malmqvist, L. M. Weiner, and J. D. Marks. 1996. Isolation of high-affinity monomeric human anti-c-erbB-2 single chain Fv using affinity-driven selection. J Mol Biol 255: 28-43.
40. Solnick, J. V., L. M. Hansen, N. R. Salama, J. K. Boonjakuakul, and M. Syvanen. 2004. Modification of *Helicobacter pylori* outer membrane protein expression during experimental infection of rhesus macaques. Proc Natl Acad Sci USA 101:2106-2111.
41. Tesar, M., C. Beckmann, P. Rottgen, B. Haase, U. Faude, and K. N. Timmis. 1995. Monoclonal antibody against pIII of filamentous phage: an immunological tool to study pIII fusion protein expression in phage display systems. Immunotechnology 1:53-64.
42. Welschof, M., P. Terness, F. Kolbinger, M. Zewe, S. Dubel, H. Dorsam, C. Hain, M. Finger, M. Jung, G. Moldenhauer, and et al. 1995. Amino acid sequence based PCR primers for amplification of rearranged human heavy and light chain immunoglobulin variable region genes. J Immunol Methods 179:203-214.
43. Xu, H. T., Y. F. Zhao, Z. X. Lian, B. L. Fan, Z. H. Zhao, S. Y. Yu, Y. P. Dai, L. L. Wang, H. L. Niu, N. Li, L. Hammarstrom, T. Boren, and R. Sjostrom. 2004. Effects of fucosylated milk of goat and mouse on *Helicobacter pylori* binding to Lewis b antigen. World J Gastroenterol 10:2063-2066.
44. Yamaoka, Y., J. Souchek, S. Odenbreit, R. Haas, A. Arnqvist, T. Boren, T. Kodama, M. S. Osato, O. Gutierrez, J. G. Kim, and D. Y. Graham. 2002. Discrimination between cases of duodenal ulcer and gastritis on the basis of putative virulence factors of *Helicobacter pylori*. J Clin Microbiol 40:2244-2246

What is claimed is:

1. A purified and isolated specific variable antibody binding region exhibiting specific activity to the native and conformational dependent BabA antigen expressed by *H. pylori* wherein the antibody is a fully human immunoglobulin IgG1 antibody comprising an Abba3 variable heavy chain region with the amino acid sequence (SEQ ID NO:18) and a variable light chain region with the amino acid sequence (SEQ ID NO:19), and said antibody neutralizes *H. pylori* by specifically binding to the native BabA protein.

2. A purified and isolated antibody Abba3, deposited as DSM19101.

3. A detection kit for detection of *H. pylori* in faecal samples, comprising: an immunoassay technique in combination with a label that is conjugated with an Abba3 antibody.

* * * * *